(12) United States Patent
Fukazawa et al.

(10) Patent No.: US 12,364,386 B2
(45) Date of Patent: Jul. 22, 2025

(54) MEDICAL IMAGE GENERATION APPARATUS, MEDICAL IMAGE GENERATION METHOD, AND MEDICAL IMAGE GENERATION PROGRAM

(71) Applicant: Sony Group Corporation, Tokyo (JP)

(72) Inventors: Kentaro Fukazawa, Tokyo (JP); Takanori Fukazawa, Tokyo (JP); Takashi Yamaguchi, Tokyo (JP); Seiji Wada, Tokyo (JP)

(73) Assignee: Sony Group Corporation, Tokyo (JP)

( * ) Notice: Subject to any disclaimer, the term of this patent is extended or adjusted under 35 U.S.C. 154(b) by 372 days.

(21) Appl. No.: 17/790,125

(22) PCT Filed: Dec. 23, 2020

(86) PCT No.: PCT/JP2020/048316
§ 371 (c)(1),
(2) Date: Jun. 30, 2022

(87) PCT Pub. No.: WO2021/140923
PCT Pub. Date: Jul. 15, 2021

(65) Prior Publication Data
US 2023/0047294 A1 Feb. 16, 2023

(30) Foreign Application Priority Data
Jan. 7, 2020 (JP) .................. 2020-001051

(51) Int. Cl.
*G06T 5/00* (2024.01)
*A61B 1/00* (2006.01)
(Continued)

(52) U.S. Cl.
CPC ........ *A61B 1/043* (2013.01); *A61B 1/000095* (2022.02); *G06T 5/50* (2013.01);
(Continued)

(58) Field of Classification Search
CPC .................................................. G06T 7/0012
See application file for complete search history.

(56) References Cited

U.S. PATENT DOCUMENTS

2009/0129626 A1* 5/2009 Hwang .................. H04N 23/71
382/100
2009/0268010 A1 10/2009 Zhao et al.
(Continued)

FOREIGN PATENT DOCUMENTS

| CN | 110099599 A | 8/2019 |
|----|----|----|
| JP | 2010-51350 A | 3/2010 |

(Continued)

OTHER PUBLICATIONS

International Search Report and Written Opinion mailed on Feb. 16, 2021, received for PCT Application PCT/JP2020/048316, filed on Dec. 23, 2020, 8 pages including English Translation.

*Primary Examiner* — Di Xiao
(74) *Attorney, Agent, or Firm* — XSENSUS LLP

(57) ABSTRACT

To generate a medical image with high visibility in fluorescence observation. A medical image generation apparatus (100) according to the present application includes an acquisition unit (131), a calculation unit (132), and a generation unit (134). An acquisition unit (131) acquires a first medical image captured with fluorescence of a predetermined wavelength and a second medical image captured with fluorescence of a wavelength different from the predetermined wavelength. A calculation unit (132) calculates a degree of scattering, indicating a degree of blurring of fluorescence of a living body, included in the first medical image and the second medical image acquired by the acquisition unit (131). A generation unit (134) generates an output image on the basis of at least one of the degrees of scattering calculated by the calculation unit (132).

20 Claims, 24 Drawing Sheets

(51) Int. Cl.
*A61B 1/04* (2006.01)
*G06T 5/50* (2006.01)
*A61B 1/313* (2006.01)

(52) U.S. Cl.
CPC ... *A61B 1/3132* (2013.01); *G06T 2207/10064* (2013.01); *G06T 2207/30101* (2013.01)

(56) References Cited

U.S. PATENT DOCUMENTS

| | | |
|---|---|---|
| 2016/0278678 A1 | 9/2016 | Valdes |
| 2019/0293620 A1* | 9/2019 | Farkas ............... G01N 21/3563 |
| 2021/0166361 A1* | 6/2021 | Fukushi ................. H04N 23/95 |

FOREIGN PATENT DOCUMENTS

| | | | | |
|---|---|---|---|---|
| JP | 2018-175762 A | | 11/2018 | |
| JP | 2020151403 A | * | 9/2020 | ......... A61B 1/00009 |
| WO | WO-2018061414 A1 | * | 4/2018 | ......... A61B 1/00009 |

* cited by examiner

FIG. 6
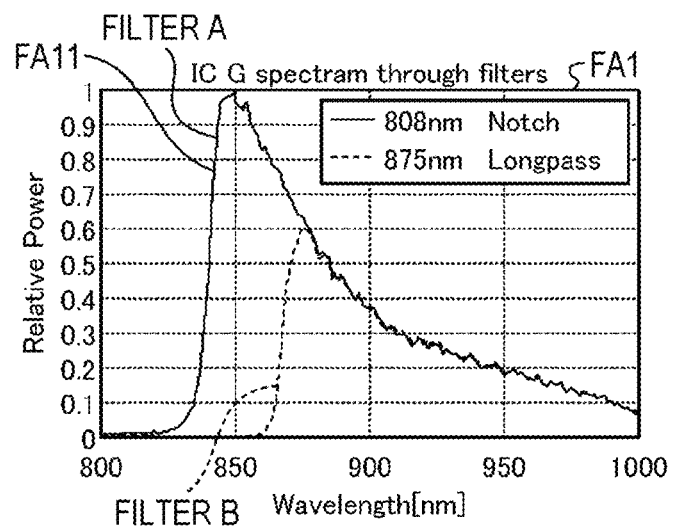
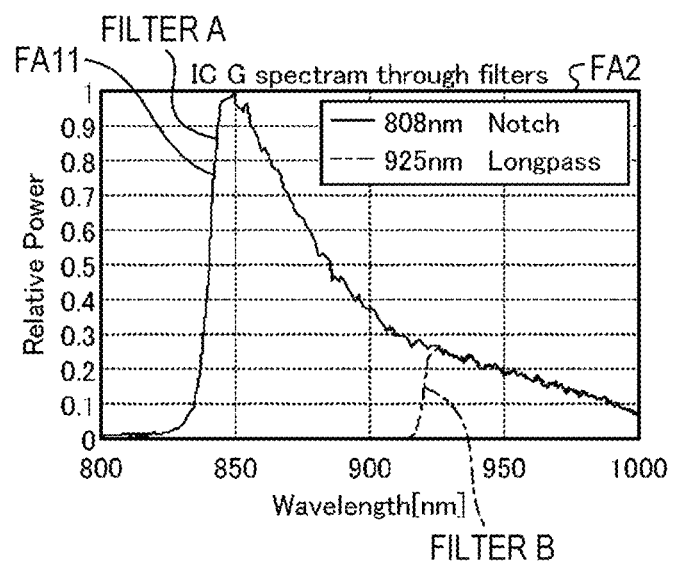
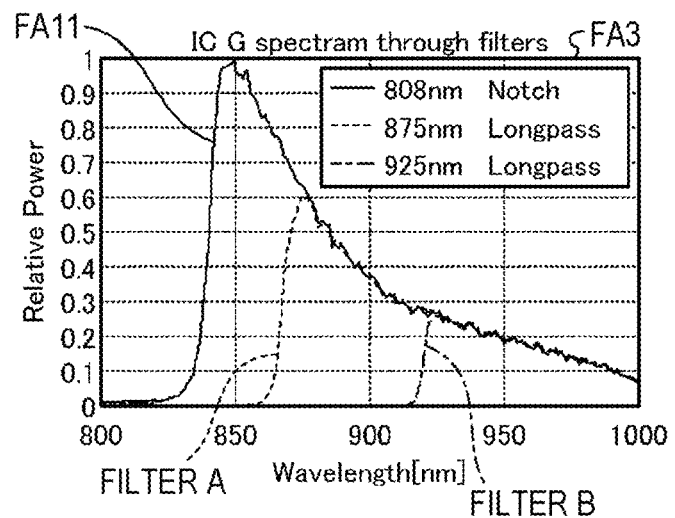

| MEDICAL IMAGE CHARACTERISTICS | ADVANTAGE (MERIT) | DISADVANTAGE (DEMERIT) |
|---|---|---|
| SHORT WAVELENGTH | LOW NOISE | HIGH SCATTERING |
| LONG WAVELENGTH | LOW SCATTERING | HIGH NOISE |

MEDICAL IMAGE GENERATION APPARATUS, MEDICAL IMAGE GENERATION METHOD, AND MEDICAL IMAGE GENERATION PROGRAM

The present application is based on PCT filing PCT/JP2020/048316, filed Dec. 23, 2020, which claims priority to Japanese Application No. 2020-001051, filed Jan. 7, 2020, the entire contents of each are incorporated herein by reference.

TECHNICAL FIELD

The present invention relates to a medical image generation apparatus, a medical image generation method, and a medical image generation program.

BACKGROUND ART

In the medical field, a lesion or the like may be visually recognized by a doctor or the like viewing a special light image captured by irradiating a living body with special light (for example, near infrared light) having a specific wavelength band. However, the special light image captured with the special light having a narrower wavelength band than the white light is generally darker than the white light image, and there is a case where it is difficult to visually recognize weak fluorescence in the deep part of the living body, or the like.

In order to promote this improvement in visibility, a technique of acquiring medical images having different wavelengths and generating an output image from the medical images is known. Specifically, a technique of generating an output image by controlling a combination ratio according to a luminance ratio of medical images having different wavelengths is known.

CITATION LIST

Patent Document

Patent Document 1: Japanese Patent Application Laid-Open No. 2018-175762

SUMMARY OF THE INVENTION

Problems to be Solved by the Invention

However, in a case where the output image is generated by the above-described method, the combination ratio of the medical image having a short wavelength, which is a brighter medical image, among the medical images having different wavelengths is high, a medical image having a large degree of scattering is generated, and the visibility of the deep part of the living body may be lowered.

The present application has been made in view of the above, and proposes a medical image generation apparatus, a medical image generation method, and a medical image generation program capable of generating a medical image with high visibility in fluorescence observation.

Solution to Problems

A medical image generation apparatus according to the present application includes an acquisition unit that acquires a first medical image captured with fluorescence of a predetermined wavelength and a second medical image captured with fluorescence of a wavelength different from the predetermined wavelength, a calculation unit that calculates a degree of scattering indicating a degree of blur of fluorescence of a living body included in the first medical image and the second medical image acquired by the acquisition unit, and a generation unit configured to generate an output image on the basis of at least one of the degrees of scattering calculated by the calculation unit.

BRIEF DESCRIPTION OF DRAWINGS

FIG. 6 is a diagram illustrating an example of a wavelength band transmitted by the filter according to the embodiment.

MODE FOR CARRYING OUT THE INVENTION

Figure 1:
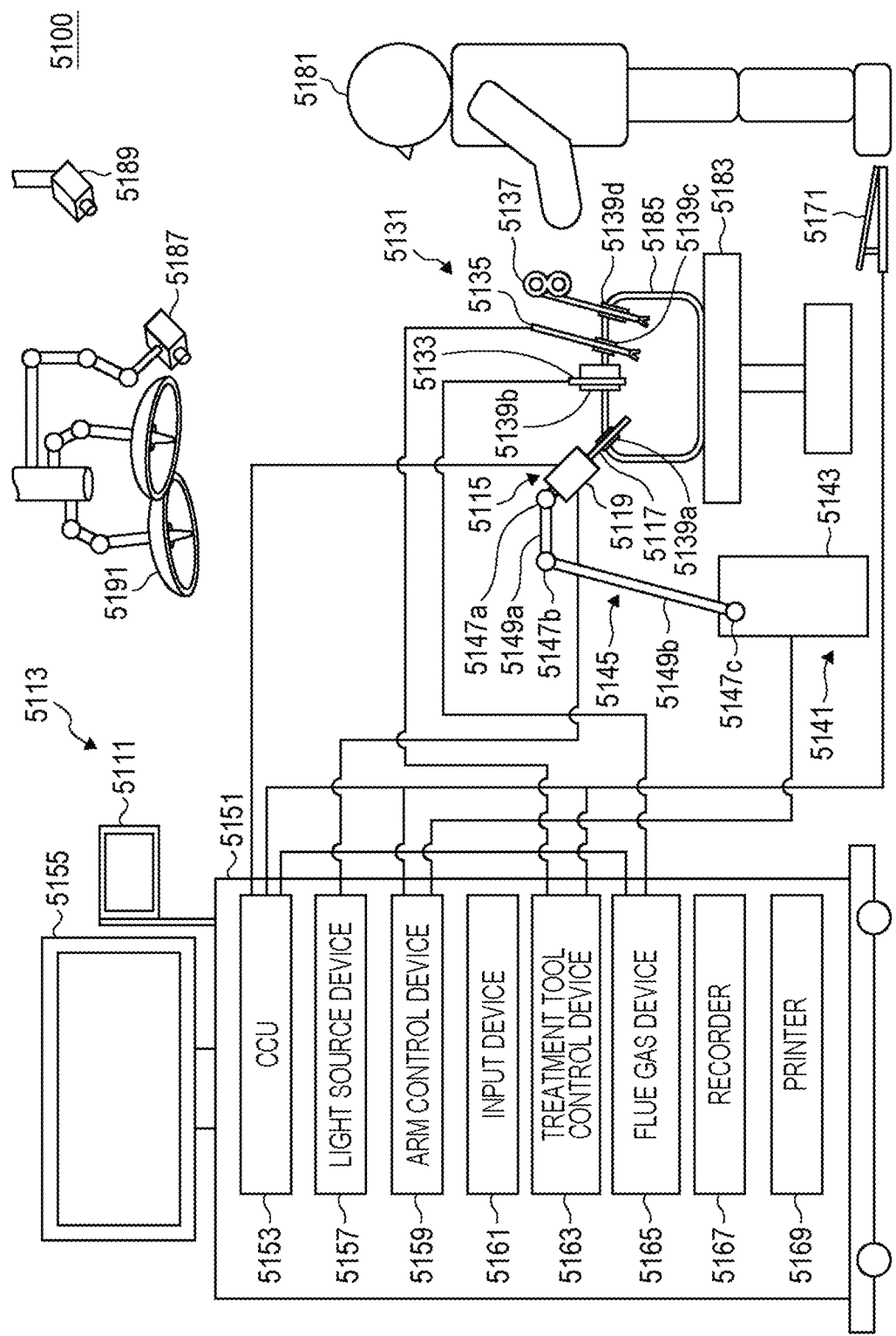
FIG. 1 is a diagram illustrating an example of a state of surgery to which an operating room system using a technical idea according to an embodiment is applied.

Hereinafter, modes (hereinafter referred to as an "embodiment") for implementing a medical image generation apparatus, a medical image generation method, and a medical image generation program according to the present application will be described in detail with reference to the drawings. Note that the medical image generation apparatus, the medical image generation method, and the medical image generation program according to the present application are not limited by the embodiments. Furthermore, in the following embodiments, the same parts are denoted by the same reference numerals, and redundant description will be omitted.

The present disclosure will be described according to the following order of items.

1. Application example
2. Configuration of system according to embodiment
3. Example of information processing
3.1. Medical image generation apparatus
3.2. Processing procedure
4. Modifications
4.1. Modification 1: Case of bringing degrees of scattering close
4.1.1. Medical image generation apparatus
4.1.2. Generation of output image using inverse filter coefficient
4.2. Modification 2: Generation of output image on the basis of difference in degrees of scattering
4.2.1. Medical image generation apparatus
4.2.2. Processing procedure
4.3. Modification 3: Visualization of scattering suppression effect in output image
4.3.1. Medical image generation apparatus
4.3.2. Processing procedure
5. Process variations
5.1. Removal of blur for each region and each pixel
5.2. Information processing in a case where blur width is less than predetermined threshold value
5.3. Calculation of degree of scattering using learning model
5.4. Fluorescence example other than ICG fluorescence
5.5. Limitation by spectroscopic plate
5.6. Filter strength
6. Hardware configuration
7. Others Embodiment 1. Application Example Application examples of the technical idea common to the embodiments of the present disclosure will be described. FIG. 1 is a diagram illustrating an example of a state of surgery to which an operating room system 5100 using a technical idea according to the present disclosure is applied. A ceiling camera 5187 and an operating room camera 5189 are provided on the ceiling of the operating room, and can image the hands of an operator (doctor) 5181 who performs treatment on an affected part of a patient 5185 on a patient bed 5183 and the entire operating room. The ceiling camera 5187 and the operating room camera 5189 each can include a magnification adjustment function, a focal length adjustment function, an imaging direction adjustment function, and the like. An illumination 5191 is provided on the ceiling of the operating room and illuminates at least the hands of the operator 5181. The illumination 5191 may be capable of appropriately adjusting the irradiation light amount, the wavelength (color) of the irradiation light, the irradiation direction of the light, and the like.

An endoscopic surgery system 5113, the patient bed 5183, the ceiling camera 5187, the operating room camera 5189, and the illumination 5191 are connected to be able to cooperate with each other via an audiovisual controller and an operating room control device (not illustrated). A centralized operation panel 5111 is provided in the operating room, and the user can appropriately operate these devices in the operating room via the centralized operation panel 5111.

Hereinafter, a configuration of the endoscopic surgery system 5113 will be described in detail. As illustrated, the endoscopic surgery system 5113 includes an endoscope 5115, other surgical tools 5131, a support arm device 5141 that supports the endoscope 5115, and a cart 5151 on which various devices for endoscopic surgery are mounted.

In endoscopic surgery, instead of cutting and opening the abdominal wall, a plurality of cylindrical puncture instruments called trocars 5139*a* to 5139*d* is punctured into the abdominal wall. Then, a lens barrel 5117 of the endoscope 5115 and the other surgical tools 5131 are inserted into the body cavity of the patient 5185 from the trocars 5139*a* to 5139*d*. In the illustrated example, as the other surgical tools 5131, a tube 5133, an energy treatment tool 5135, and a forceps 5137 are inserted into the body cavity of the patient 5185. Here, the tube 5133 may be configured to exhaust smoke generated in the body cavity to the outside of the body cavity. Furthermore, on the other hand, the tube 5133 may have a function of injecting gas into the body cavity to inflate the body cavity. Furthermore, the energy treatment tool 5135 is a treatment tool for performing incision and detachment of tissue, sealing of a blood vessel, or the like by high-frequency current or ultrasonic vibration. However, the illustrated surgical tools 5131 are merely an example, and various surgical tools generally used in endoscopic surgery, such as tweezers and a retractor may be used as the surgical tools 5131.

An image of the surgical part in the body cavity of the patient 5185 captured by the endoscope 5115 is displayed on a display device 5155. While viewing the image of the surgical part displayed on the display device 5155 in real time, the operator 5181 performs treatment such as resection of an affected part using the energy treatment tool 5135 and the forceps 5137. Note that, although not illustrated, the tube 5133, the energy treatment tool 5135, and the forceps 5137 are supported by the operator 5181, an assistant, or the like during surgery.

Support Arm Device

The support arm device 5141 includes an arm unit 5145 extending from a base unit 5143. In the illustrated example, the arm unit 5145 includes joint units 5147a, 5147b, and 5147c and links 5149a and 5149b, and is driven under the control of an arm control device 5159. The endoscope 5115 is supported by the arm unit 5145, and its position and posture are controlled. As a result, stable fixation of the position of the endoscope 5115 can be implemented.

Endoscope

The endoscope 5115 includes the lens barrel 5117 whose region of a predetermined length from the distal end is inserted into the body cavity of the patient 5185, and a camera head 5119 connected to the proximal end of the lens barrel 5117. In the illustrated example, the endoscope 5115 configured as a so-called rigid scope including the rigid lens barrel 5117 is illustrated, but the endoscope 5115 may be configured as a so-called flexible scope including the flexible lens barrel 5117.

An opening portion into which an objective lens is fitted is provided at the distal end of the lens barrel 5117. A light source device 5157 is connected to the endoscope 5115, and light generated by the light source device 5157 is guided to the distal end of the lens barrel by a light guide extending inside the lens barrel 5117, and is emitted toward an observation target in the body cavity of the patient 5185 via the objective lens. Note that the endoscope 5115 may be a forward-viewing endoscope, an oblique-viewing endoscope, or a side-viewing endoscope.

An optical system and an imaging element are provided inside the camera head 5119, and reflected light (observation light) from the observation target is condensed on the imaging element by the optical system. The observation light is photoelectrically converted by the imaging element, and an electric signal corresponding to the observation light, that is, an image signal corresponding to the observation image, is generated. The image signal is transmitted to a camera control unit (CCU) 5153 as RAW data. Note that the camera head 5119 has a function of adjusting the magnification and the focal length by appropriately driving the optical system.

Note that, for example, in order to cope with stereoscopic viewing (3D display) or the like, a plurality of imaging elements may be provided in the camera head 5119. In this case, a plurality of relay optical systems is provided inside the lens barrel 5117 in order to guide the observation light to each of the plurality of imaging elements.

Various Devices Mounted on Cart

The CCU 5153 includes a central processing unit (CPU), a graphics processing unit (GPU), and the like, and integrally controls operation of the endoscope 5115 and the display device 5155. Specifically, the CCU 5153 performs, on an image signal received from the camera head 5119, various types of image processing for displaying an image on the basis of the image signal, such as development processing (demosaic processing), for example. The CCU 5153 provides the image signal subjected to the image processing to the display device 5155. Furthermore, the audiovisual controller described above is connected to the CCU 5153. The CCU 5153 also provides the image signal subjected to the image processing to an audiovisual controller 5107. Furthermore, the CCU 5153 transmits a control signal to the camera head 5119 and controls driving thereof. The control signal can include information regarding imaging conditions such as magnification and focal length. The information regarding the imaging conditions may be input via an input device 5161 or may be input via the centralized operation panel 5111 described above.

The display device 5155 displays an image based on the image signal subjected to the image processing by the CCU 5153 under the control of the CCU 5153. In a case where the endoscope 5115 is compatible with high-resolution imaging such as 4K (the number of horizontal pixels 3840×the number of vertical pixels 2160) or 8K (the number of horizontal pixels 7680×the number of vertical pixels 4320), and/or in a case where the endoscope is compatible with 3D display, for example, a display device capable of performing high-resolution display and/or a display device capable of performing 3D display can be used as the display device 5155, respectively. In a case where the display device is compatible with high resolution imaging such as 4K or 8K, a further immersive feeling can be obtained by using a display device having a size of 55 inches or more as the display device 5155. Furthermore, a plurality of display devices 5155 having different resolutions and sizes may be provided depending on the application.

The light source device 5157 includes a light source such as a light emitting diode (LED), for example, and supplies irradiation light for imaging a surgical part to the endoscope 5115.

The arm control device 5159 includes, for example, a processor such as a CPU, and operates according to a predetermined program to control driving of the arm unit 5145 of the support arm device 5141 according to a predetermined control method.

The input device 5161 is an input interface for the endoscopic surgery system 5113. The user can input various types of information to the endoscopic surgery system 5113 via the input device 5161 and input instructions. For example, the user inputs various types of information regarding surgery, such as physical information of a patient and information regarding a surgical procedure of the surgery, via the input device 5161. Furthermore, for example, the user inputs an instruction for driving the arm unit 5145, an instruction for changing imaging conditions (type, magnification, focal length, and the like of irradiation light) by the endoscope 5115, an instruction for driving the energy treatment tool 5135, and the like via the input device 5161.

The type of the input device 5161 is not limited, and the input device 5161 may be a known input device. Examples of the input device 5161 can include a mouse, a keyboard, a touch panel, a switch, a foot switch 5171, a lever, and/or the like. In a case where the input device 5161 includes a touch panel, the touch panel may be provided on the display face of the display device 5155.

Alternatively, the input device 5161 is a device worn by the user, for example, a glasses-type wearable device, a head mounted display (HMD), or the like, and various inputs are performed according to a gesture or a line of sight of the user detected by these devices. Furthermore, the input device 5161 includes a camera capable of detecting movement of the user, and various inputs are performed according to a gesture or a line of sight of the user detected from a video captured by the camera. Moreover, the input device 5161 includes a microphone capable of collecting user's voice, and various inputs are performed by voice via the microphone. As described above, the input device 5161 is configured to be able to input various types of information in a non-contact manner, and thus, in particular, a user (for example, the operator 5181) belonging to a clean area can operate a device belonging to an unclean area in a non-contact manner. In addition, since the user can operate the device without releasing his/her hand from the possessed surgical tool, the convenience of the user is improved.

A treatment tool control device 5163 controls driving of the energy treatment tool 5135 for cauterization and incision of tissue, sealing of a blood vessel, or the like. A flue gas device 5165 feeds gas into the body cavity of the patient 5185 via the tube 5133 in order to inflate the body cavity for the purpose of securing a visual field by the endoscope 5115 and securing a working space of the operator. In addition, the flue gas device 5165 has a function of exhausting flue gas generated in the body cavity in order to secure a visual field by the endoscope 5115. A recorder 5167 is a device capable of recording various types of information regarding surgery. A printer 5169 is a device capable of printing various types of information regarding surgery in various formats such as text, image, or graph.

Hereinafter, a particularly characteristic configuration of the endoscopic surgery system 5113 will be described in more detail.

Support Arm Device

The support arm device 5141 includes the base unit 5143 which is a base, and the arm unit 5145 extending from the base unit 5143. In the illustrated example, the arm unit 5145 includes the plurality of joint units 5147a, 5147b, and 5147c and the plurality of links 5149a and 5149b connected by the joint unit 5147b, but in FIG. 1, the configuration of the arm unit 5145 is illustrated in a simplified manner for the sake of simplicity. Actually, the shapes, the number, and the arrangement of the joint units 5147a to 5147c and the links 5149a and 5149b, the directions of the rotation axes of the joint units 5147a to 5147c, and the like can be appropriately set so that the arm unit 5145 has a desired degree of freedom. For example, the arm unit 5145 can be suitably configured to have 6 degrees of freedom or more. As a result, since the endoscope 5115 can be freely moved within the movable range of the arm unit 5145, the lens barrel 5117 of the endoscope 5115 can be inserted into the body cavity of the patient 5185 from a desired direction.

The joint units 5147a to 5147c include actuators, and the joint units 5147a to 5147c are configured to be rotatable around a predetermined rotation axis by driving of the actuators. The driving of the actuators is controlled by the arm control device 5159, whereby the rotation angle of each of the joint units 5147a to 5147c is controlled, and the driving of the arm unit 5145 is controlled. As a result, control of the position and posture of the endoscope 5115 can be implemented. At this time, the arm control device 5159 can control the driving of the arm unit 5145 by various known control methods such as force control or position control.

For example, since the operator 5181 appropriately performs an operation input via the input device 5161 (including the foot switch 5171), the driving of the arm unit 5145 may be appropriately controlled by the arm control device 5159 according to the operation input, and the position and posture of the endoscope 5115 may be controlled. With this control, the endoscope 5115 at the distal end of the arm unit 5145 can be moved from an any position to an any position and then fixedly supported at the position after the movement. Note that the arm unit 5145 may be operated by a so-called master-slave method. In this case, the arm unit 5145 can be remotely operated by the user via the input device 5161 installed at a place away from the operating room.

Furthermore, in a case where the force control is applied, the arm control device 5159 may perform so-called power assist control in which the actuator of each of the joint units 5147a to 5147c is driven so that an external force is received from the user and the arm unit 5145 smoothly moves according to the external force. As a result, when the user moves the arm unit 5145 while directly touching the arm unit 5145, the arm unit 5145 can be moved with a relatively small force. Therefore, it is possible to more intuitively move the endoscope 5115 with a simpler operation, and the convenience of the user can be improved.

Here, in general, in endoscopic surgery, the endoscope 5115 is supported by a doctor called scopist. On the other hand, it is possible to more reliably fix the position of the endoscope 5115 without manual operation by using the support arm device 5141, so that it is possible to stably obtain an image of the surgical part and smoothly perform the surgery.

Note that the arm control device 5159 is not necessarily provided on the cart 5151. Furthermore, the arm control device 5159 is not necessarily one device. For example, the arm control device 5159 may be provided in each of the joint units 5147a to 5147c of the arm unit 5145 of the support arm device 5141, and the drive control of the arm unit 5145 may be implemented by the plurality of arm control devices 5159 cooperating with each other.

Light Source Device

The light source device 5157 supplies the endoscope 5115 with irradiation light for imaging the surgical part. The light source device 5157 includes, for example, an LED, a laser light source, or a white light source including a combination thereof. At this time, in a case where the white light source is configured by a combination of RGB laser light sources, the output intensity and the output timing of each color (each wavelength) can be controlled with high accuracy, so that the white balance of the captured image can be adjusted in the light source device 5157. Furthermore, in this case, it is also possible to capture an image corresponding to each RGB in a time division manner by irradiating the observation target with the laser light from each of the RGB laser light sources in a time division manner and controlling the driving of the imaging element of the camera head 5119 in synchronization with the irradiation timing. According to this method, a color image can be obtained without providing a color filter in the imaging element.

Furthermore, the driving of the light source device 5157 may be controlled so as to change the intensity of light to be output every predetermined time. It is possible to generate an image with a high dynamic range without so-called underexposure areas and overexposure areas by controlling the driving of the imaging element of the camera head 5119 in synchronization with the timing of the change in the light intensity to acquire images in a time division manner and combining the images.

Furthermore, the light source device 5157 may be configured to be able to supply light in a predetermined wavelength band corresponding to special light observation. In the special light observation, for example, so-called narrow band imaging is performed in which a predetermined tissue such as a blood vessel in a mucosal surface layer is imaged with high contrast by radiating light in a narrower band than that of irradiation light (that is, white light) at the time of normal observation using wavelength dependency of light absorption in a body tissue. Alternatively, in the special light observation, fluorescence observation for obtaining an image by fluorescence generated by irradiation with excitation light may be performed. In the fluorescence observation, for example, fluorescence from a body tissue can be observed by irradiating the body tissue with excitation light (autofluorescence observation), or a fluorescent image can be obtained by locally injecting a reagent such as indocyanine green (ICG) into a body tissue and irradiating the body tissue with excitation light corresponding to a fluorescence wavelength of the reagent. The light source device 5157 can be configured to be able to supply narrow band light and/or excitation light corresponding to such special light observation.

Camera Head and CCU

Figure 2:
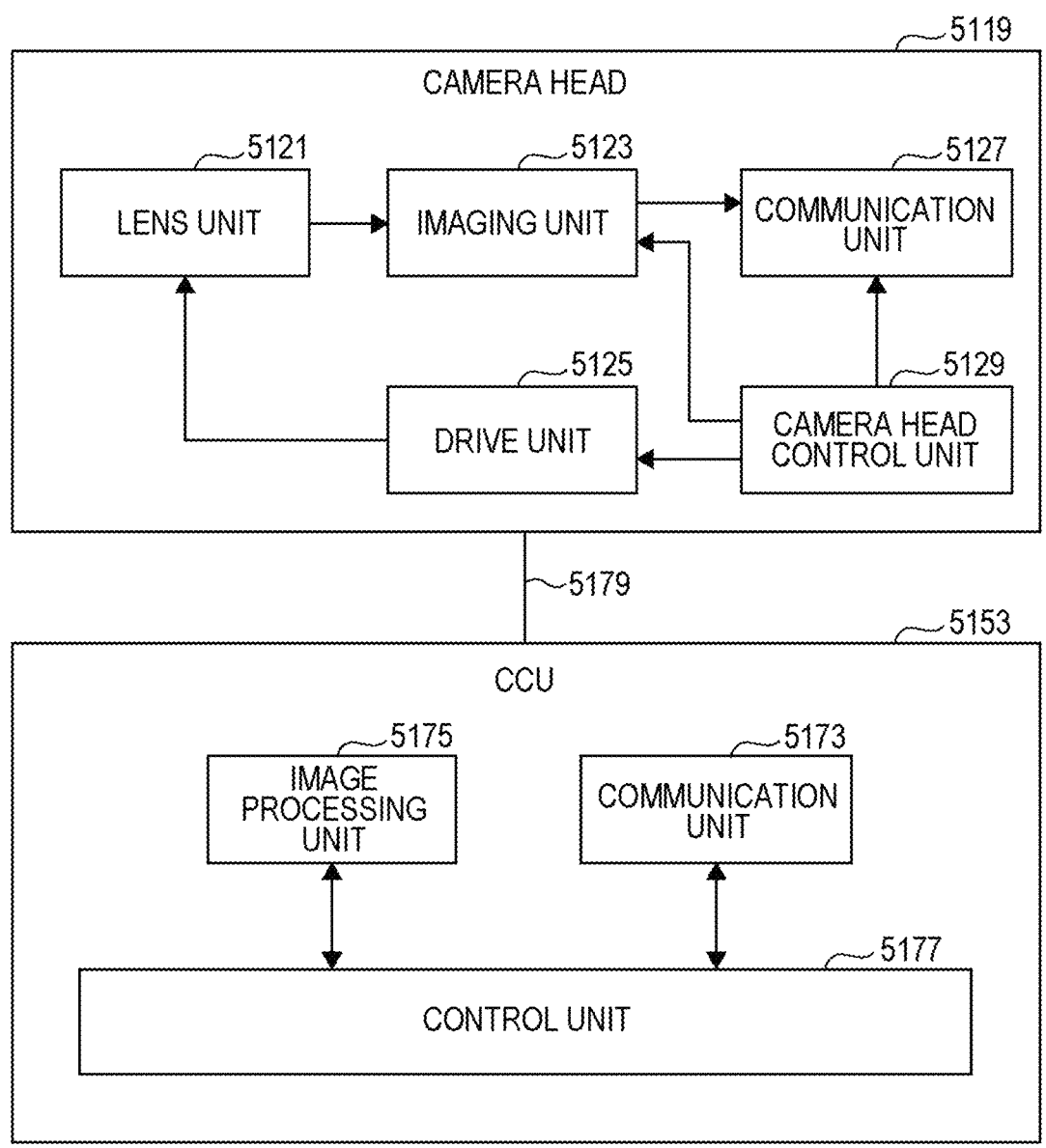
FIG. 2 is a block diagram illustrating an example of a functional configuration of a camera head and a CCU illustrated in FIG. 1.

The functions of the camera head 5119 and the CCU 5153 of the endoscope 5115 will be described in more detail with reference to FIG. 2. FIG. 2 is a block diagram illustrating an example of functional configurations of the camera head 5119 and the CCU 5153 illustrated in FIG. 1.

Referring to FIG. 2, the camera head 5119 includes, as its functions, a lens unit 5121, an imaging unit 5123, a drive unit 5125, a communication unit 5127, and a camera head control unit 5129. Furthermore, the CCU 5153 includes, as its functions, a communication unit 5173, an image processing unit 5175, and a control unit 5177. The camera head 5119 and the CCU 5153 are connected to be bidirectionally communicable by a transmission cable 5179.

First, a functional configuration of the camera head 5119 will be described. The lens unit 5121 is an optical system provided at a connection portion with the lens barrel 5117. Observation light taken in from the distal end of the lens barrel 5117 is guided to the camera head 5119 and enters the lens unit 5121. The lens unit 5121 is configured by combining a plurality of lenses including a zoom lens and a focus lens. The optical characteristics of the lens unit 5121 are adjusted so as to condense the observation light on the light receiving face of the imaging element of the imaging unit 5123. Further, the zoom lens and the focus lens are configured such that its position on the optical axis is movable in order to adjust the magnification and the focal point of the captured image.

The imaging unit 5123 includes an imaging element and is disposed behind the lens unit 5121. The observation light having passed through the lens unit 5121 is condensed on the light receiving face of the imaging element, and an image signal corresponding to the observation image is generated by photoelectric conversion. The image signal generated by the imaging unit 5123 is provided to the communication unit 5127.

The imaging element constituting the imaging unit 5123, for example, includes a complementary metal oxide semiconductor (CMOS) type image sensor having a Bayer array and capable of performing color imaging. Note that the imaging element may, for example, include an imaging element that can cope with capturing of a high-resolution image of 4K or more. The operator 5181 can grasp the state of the surgical part in more detail by obtaining the image of the surgical part with high resolution, and can perform the surgery more smoothly.

Furthermore, the imaging element constituting the imaging unit 5123 is configured to include a pair of imaging elements for acquiring respective image signals for the right eye and the left eye corresponding to 3D display. The operator 5181 can more accurately grasp the depth of the living tissue in the surgical part by performing the 3D display. Note that, in a case where the imaging unit 5123 is configured as a multi-plate type, a plurality of lens units 5121 is provided corresponding to respective imaging elements.

Furthermore, the imaging unit 5123 is not necessarily provided on the camera head 5119. For example, the imaging unit 5123 may be provided immediately after the objective lens inside the lens barrel 5117.

The drive unit 5125 includes an actuator, and moves the zoom lens and the focus lens of the lens unit 5121 by a predetermined distance along the optical axis under the control of the camera head control unit 5129. As a result, the magnification and focus of the image captured by the imaging unit 5123 can be appropriately adjusted.

The communication unit 5127 includes a communication device for transmitting and receiving various types of information to and from the CCU 5153. The communication unit 5127 transmits the image signal obtained from the imaging unit 5123 as RAW data to the CCU 5153 via the transmission cable 5179. At this time, the image signal is preferably transmitted through optical communication in order to display the captured image of the surgical part with low latency. This is because, at the time of surgery, the operator 5181 performs surgery while observing the state of the affected part with the captured image, and thus, for safer and more reliable surgery, it is required to display a moving image of the surgical part in real time as much as possible. In a case where optical communication is performed, the communication unit 5127 includes a photoelectric conversion module that converts an electric signal into an optical signal. The image signal is converted into an optical signal by the photoelectric conversion module and then transmitted to the CCU 5153 via the transmission cable 5179.

Furthermore, the communication unit 5127 receives, from the CCU 5153, a control signal for controlling driving of the camera head 5119. The control signal includes, for example, information regarding imaging conditions such as information for specifying a frame rate of a captured image, information for specifying an exposure value at the time of imaging, and/or information for specifying a magnification and a focus of a captured image. The communication unit 5127 provides the received control signal to the camera head control unit 5129. Note that the control signal from the CCU 5153 may also be transmitted through optical communication. In this case, the communication unit 5127 includes a photoelectric conversion module that converts an optical signal into an electric signal, and the control signal is converted into an electric signal by the photoelectric conversion module and then supplied to the camera head control unit 5129.

Note that the imaging conditions such as the frame rate, the exposure value, the magnification, and the focus are automatically set by the control unit 5177 of the CCU 5153 on the basis of the acquired image signal. That is, the endoscope 5115 has a so-called auto exposure (AE) function, an auto focus (AF) function, and an auto white balance (AWB) function.

The camera head control unit 5129 controls driving of the camera head 5119 on the basis of the control signal, from the CCU 5153, received via the communication unit 5127. For example, the camera head control unit 5129 controls driving of the imaging element of the imaging unit 5123 on the basis of the information for designating the frame rate of the captured image and/or the information for designating the exposure at the time of imaging. Furthermore, for example, the camera head control unit 5129 appropriately moves the zoom lens and the focus lens of the lens unit 5121 via the drive unit 5125 on the basis of the information for designating the magnification and the focal point of the captured image. The camera head control unit 5129 may further have a function of storing information for identifying the lens barrel 5117 and the camera head 5119.

Note that the camera head 5119 can have resistance to autoclave sterilization processing with the lens unit 5121, the imaging unit 5123, and the like disposed in a sealed structure having high airtightness and waterproofness.

Next, a functional configuration of the CCU 5153 will be described. The communication unit 5173 includes a communication device for transmitting and receiving various types of information to and from the camera head 5119. The communication unit 5173 receives an image signal transmitted from the camera head 5119 via the transmission cable 5179. At this time, as described above, the image signal can be suitably transmitted through optical communication. In this case, the communication unit 5173 includes a photoelectric conversion module that converts an optical signal into an electric signal for optical communication. The communication unit 5173 supplies the image signal converted into the electric signal to the image processing unit 5175.

Furthermore, the communication unit 5173 transmits a control signal for controlling driving of the camera head 5119 to the camera head 5119. The control signal may also be transmitted through optical communication.

The image processing unit 5175 performs various types of image processing on the image signal that is RAW data transmitted from the camera head 5119. Examples of the image processing include various known signal processing such as development processing, high image quality processing (band emphasis processing, super-resolution processing, noise reduction (NR) processing, camera shake correction processing, and/or the like), and/or enlargement processing (electronic zoom processing). Furthermore, the image processing unit 5175 performs detection processing on an image signal for performing an AE, an AF, and an AWB.

The image processing unit 5175 includes a processor such as a CPU or a GPU, and the processor operates according to a predetermined program, whereby the above-described image processing and detection processing can be performed. Note that, in a case where the image processing unit 5175 includes a plurality of GPUs, the image processing unit 5175 appropriately divides information related to an image signal, and performs image processing in parallel by the plurality of GPUs.

The control unit 5177 performs various types of control related to imaging of the surgical part by the endoscope 5115 and display of the captured image. For example, the control unit 5177 generates a control signal for controlling driving of the camera head 5119. At this time, in a case where the imaging condition is input by the user, the control unit 5177 generates the control signal on the basis of the input by the user. Alternatively, in a case where the endoscope 5115 has the AE function, the AF function, and the AWB function, the control unit 5177 appropriately calculates an optimum exposure value, focal length, and white balance according to a result of the detection processing by the image processing unit 5175 to generate a control signal.

Furthermore, the control unit 5177 causes the display device 5155 to display the image of the surgical part on the basis of the image signal subjected to the image processing by the image processing unit 5175. At this time, the control unit 5177 recognizes various objects in the surgical part image using various image recognition techniques. For example, the control unit 5177 can recognize a surgical tool such as a forceps, a specific living body site, bleeding, mist at the time of using the energy treatment tool 5135, and the like by detecting the shape, color, and the like of the edge of the object included in the surgical part image. When displaying the image of the surgical part on the display device 5155, the control unit 5177 superimposes and displays various types of surgery support information on the image of the surgical part using the recognition result. The surgery support information is superimposed and displayed, and presented to the operator 5181, so that the surgery can be more safely and reliably advanced.

The transmission cable 5179 connecting the camera head 5119 and the CCU 5153 is an electric signal cable compatible with electric signal communication, an optical fiber compatible with optical communication, or a composite cable thereof.

Here, in the illustrated example, communication is performed by wire using the transmission cable 5179, but communication between the camera head 5119 and the CCU 5153 may be performed wirelessly. In a case where the communication between the two is performed wirelessly, it is not necessary to lay the transmission cable 5179 in the operating room, so that a situation in which the movement of the medical staff in the operating room is hindered by the transmission cable 5179 can be eliminated.

An example of the operating room system 5100 to which the technique according to the present disclosure can be applied is described above. Note that, here, a case where the medical system to which the operating room system 5100 is applied is the endoscopic surgery system 5113 is described as an example, but the configuration of the operating room system 5100 is not limited to such an example. For example, the operating room system 5100 may be applied to a flexible endoscope system for examination or a microscopic surgery system instead of the endoscopic surgery system 5113.

As described above, in the endoscopic surgery system described as an example in which the medical light source device is connected to the endoscope, the medical light source device (the light source device 5157 in FIG. 1) is mounted on the cart. The entire cart on which various devices including the medical light source device are mounted can be miniaturized by mounting the miniaturized medical light source device of the present technology. Moreover, the degree of freedom of the installation range of the medical light source device is increased by achieving the miniaturization of the medical light source device, and the medical light source device can be mounted on, for example, a cart, the disorder of the surgical site is eliminated, and the operation environment is better.

2. Configuration of System According to Embodiment

Figure 3:
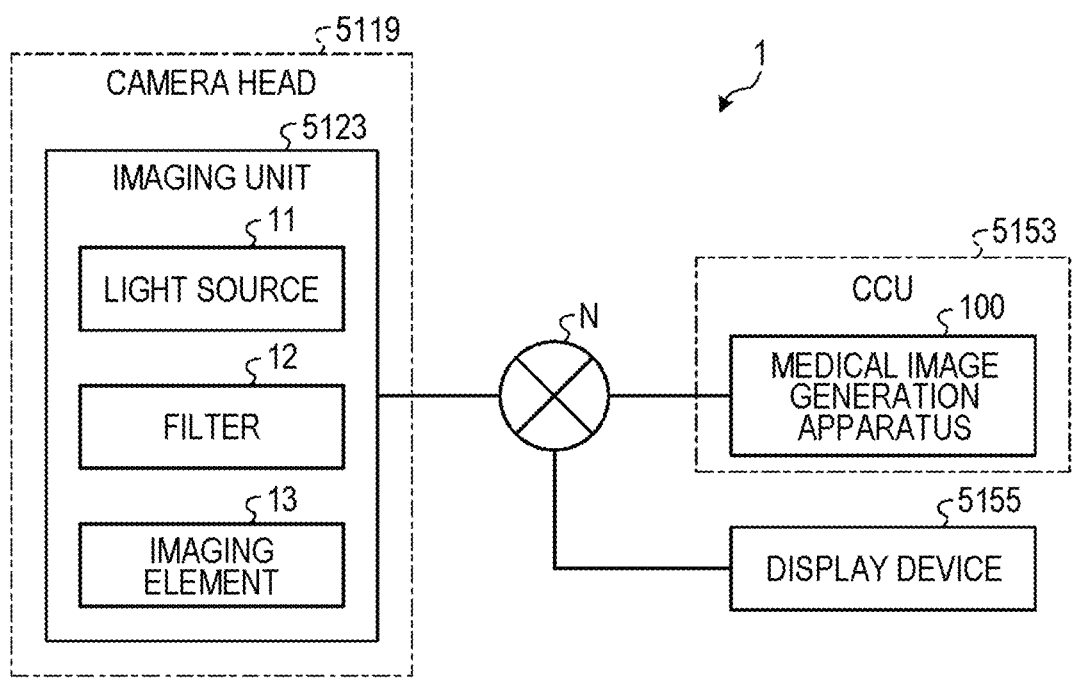
FIG. 3 is a diagram illustrating a medical image generation system 1 according to the embodiment.

A medical image generation system 1 according to the embodiment will be described with reference to FIG. 3. FIG.

3 is a diagram illustrating the medical image generation system 1 according to the embodiment. As illustrated in FIG. 3, the medical image generation system 1 includes the camera head 5119, the display device 5155, and a medical image generation apparatus 100.

The camera head 5119 supplies the captured medical image to the medical image generation apparatus 100. Other descriptions of the camera head 5119 are similar to those of the camera head 5119 in FIG. 1.

The imaging unit 5123 is a camera head type camera, and is used to image the inside of the body in a hospital or a laboratory, for example. The imaging unit 5123 uses near infrared rays to stain a dye such as ICG flowing in a blood vessel, for example. Then, the imaging unit 5123 acquires a medical image by imaging the developed fluorescence. As illustrated in FIG. 3, the imaging unit 5123 includes a light source 11, a filter 12, and an imaging element 13.

The light source 11 is a light source that emits light for developing fluorescence of a dye such as ICG. The light source 11 is, for example, a light source that emits near infrared rays.

The filter 12 is a filter that transmits only fluorescence of a specific wavelength. For example, the filter 12 is a filter that transmits a wavelength on a long wavelength side and blocks a wavelength on a short wavelength side. The filter 12 is used to transmit only fluorescence of a specific wavelength among the fluorescence developed by the light source 11. As the optical characteristics, scattering is more suppressed as the fluorescence is on the longer wavelength side, and thus, a technique of transmitting not the entire region of the fluorescence wavelength but only the fluorescence on the longer wavelength side of the fluorescence wavelength and performing imaging is conceivable. However, in the case of performing imaging with fluorescence only on the long wavelength side, the fluorescence intensity decreases, and thus the image quality of the medical image may deteriorate. In addition, the medical image is dark. Therefore, there is room for improvement in the technique of performing imaging only with the fluorescence on the long wavelength side in order to promote improvement in visibility.

The imaging element 13 is an imaging device that images an observation target in the body and acquires a medical image (for example, a pathological image). The observation target is, for example, a blood vessel, a tissue, a cell, or the like. The imaging element 13 is used to capture an image with fluorescence of a specific wavelength transmitted by the filter 12. Furthermore, the imaging element 13 transmits the acquired medical image to the medical image generation apparatus 100.

The display device 5155 receives the output image from the medical image generation apparatus 100 and displays the received output image. Other descriptions of the display device 5155 are similar to those of the display device 5155 in FIG. 1.

The medical image generation apparatus 100 is an information processing apparatus such as a PC or a work station (WS). The medical image generation apparatus 100 acquires a medical image captured by the imaging unit 5123. Specifically, the medical image generation apparatus 100 acquires medical images captured with fluorescence having different wavelengths by the imaging element 13. Then, the medical image generation apparatus 100 generates an output image on the basis of the degrees of scattering of medical images captured with fluorescence having different wavelengths. In addition, the medical image generation apparatus 100 transmits the output image to the display device 5155.

The medical image generation apparatus 100 may be, for example, the CCU 5153 as described in FIG. 1.

Here, details of the configuration of the imaging unit 5123 will be described. There are two configurations of the imaging unit 5123. The two configurations are a configuration using an imaging method based on one type of imaging element called single-plate imaging and a configuration using an imaging method based on two types of imaging elements called two-plate imaging. The imaging element may be an imaging element for capturing a visible light image or an imaging element for capturing a fluorescence image. A visible light image is generated by imaging light belonging to a visible light wavelength band on the imaging element for capturing a visible light image. Furthermore, a fluorescence image is generated by imaging light belonging to a fluorescence wavelength band on the imaging element for capturing a fluorescence image. Specifically, in a case where the imaging element is an imaging element for capturing a visible light image, light in a visible light wavelength band that has passed through the filter is coupled to the imaging element for capturing a visible light image, whereby a medical image that is a visible light image is generated. Similarly, in a case where the imaging element is an imaging element for capturing a fluorescence image, light in a fluorescence wavelength band that has passed through the filter is coupled to the imaging element for capturing a fluorescence image, whereby a medical image that is a fluorescence image is generated. Hereinafter, a configuration in which the imaging unit 5123 uses single-plate imaging and a configuration in which the imaging unit uses two-plate imaging will be described with reference to FIGS. 4 and 5. In the present embodiment, the imaging method by the imaging unit 5123 includes single-plate imaging and two-plate imaging.

Figure 4:
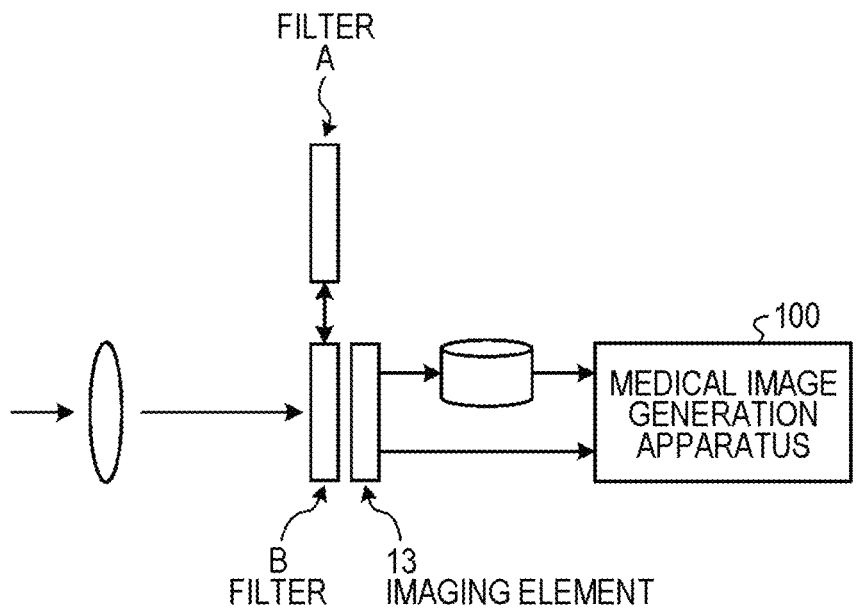
FIG. 4 is a diagram illustrating a configuration example (in the case of single-plate imaging) of an imaging unit according to the embodiment.

FIG. 4 illustrates a configuration of the imaging unit 5123 using single-plate imaging. In FIG. 4, two filters 12 (filter A and filter B) are used for one imaging element 13. In the filter A and the filter B, the fluorescence transmitted by each filter is different according to the wavelength. Fluorescence having different wavelengths is input to the imaging element 13 by periodically (for example, every predetermined time interval) switching the filter A and the filter B. Here, the filter A is a filter that transmits a short wavelength, and the filter B is a filter that transmits a long wavelength. In this case, fluorescence having a short wavelength and fluorescence having a long wavelength are separately input to the imaging element 13. Therefore, the imaging unit 5123 can acquire medical images captured with fluorescence having different wavelengths. Then, the imaging unit 5123 supplies the acquired medical images to an external information processing apparatus (for example, the medical image generation apparatus 100).

Note that, in the case of single-plate imaging, since fluorescence having different wavelengths is input to the imaging element 13 by periodically (for example, every predetermined time interval) switching the filter A and the filter B, a time difference due to switching the filter A and the filter B occurs in the input of fluorescence having different wavelengths. Therefore, it is difficult for the imaging unit 5123 to simultaneously acquire medical images captured with fluorescence having different wavelengths. In order to eliminate the limitation due to the time difference, the imaging unit 5123 temporarily stores a medical image captured with fluorescence of one of the wavelengths, so that both the medical images can be provided to the external information processing apparatus simultaneously with the acquisition of the medical image captured with the fluorescence of the other wavelength. That is, the imaging unit 5123 can simultaneously supplies the medical image captured by the filter A and the medical image captured by the filter B to the external information processing apparatus.

Figure 5:
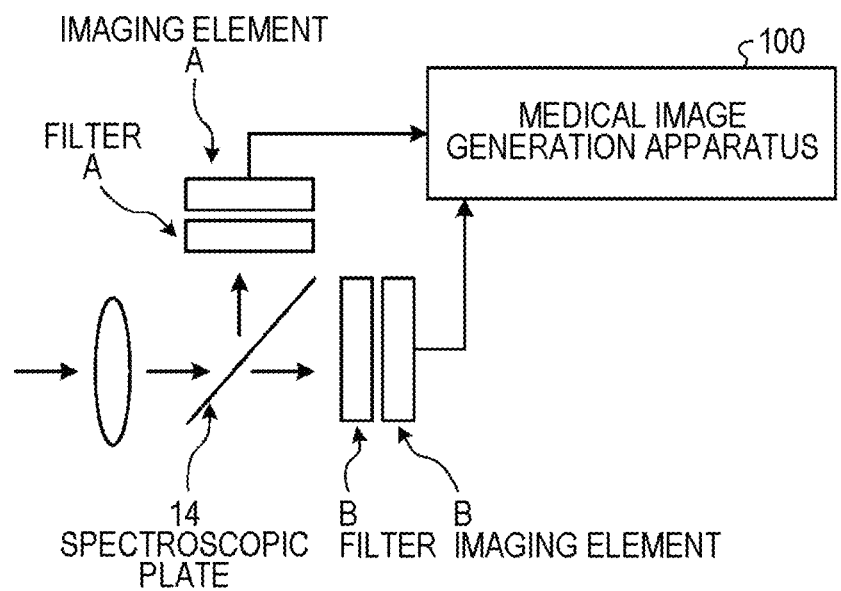
FIG. 5 is a diagram illustrating a configuration example (in the case of two-plate imaging) of the imaging unit according to the embodiment.

FIG. 5 illustrates a configuration of the imaging unit 5123 using two-plate imaging. Note that the description similar to that of the single-plate imaging will be appropriately omitted. In FIG. 5, unlike the case of single-plate imaging, two imaging elements 13 (imaging element A and imaging element B) are used for two filters 12 (filter A and filter B). Note that the two imaging elements 13 are assumed to be the same. In the case of two-plate imaging, the imaging unit 5123 includes a spectroscopic plate 14. The spectroscopic plate 14 is used to reflect fluorescence of a specific wavelength included in the fluorescence and transmit fluorescence of the other wavelengths other than the specific wavelength included in the fluorescence. The spectroscopic plate 14 is, for example, a dichroic mirror. In the imaging unit 5123, the spectroscopic plate 14 is used to reflect fluorescence of a specific wavelength among fluorescence stained by the light source 11 and transmit fluorescence of the other wavelengths other than the specific wavelength. Hereinafter, a case where the spectroscopic plate 14 reflects fluorescence having a short wavelength and transmit fluorescence having a long wavelength will be described.

In this case, the short wavelength fluorescence reflected by the spectroscopic plate 14 is transmitted through the filter A. Note that the filter A is assumed to be a filter that transmits a short wavelength. The spectroscopic plate 14 may not be able to completely reflect only fluorescence of a specific wavelength. Therefore, there may be an error in the wavelength in the short wavelength fluorescence reflected by the spectroscopic plate 14. The filter A is used to correct an error in reflection by the spectroscopic plate 14. Then, the short wavelength fluorescence transmitted through the filter A is input to the imaging element 13. In this case, the imaging element 13 acquires a medical image captured with a short wavelength. Meanwhile, the long wavelength fluorescence transmitted by the spectroscopic plate 14 is transmitted by the filter B. Note that the filter B is assumed to be a filter that transmits a long wavelength. As in the reflection, there may be an error in the wavelength in the long wavelength fluorescence transmitted by the spectroscopic plate 14. The filter B is used to correct an error in transmission by the spectroscopic plate 14. Then, the long wavelength fluorescence transmitted through the filter B is input to the imaging element 13. In this case, the imaging element 13 acquires a medical image captured with a long wavelength.

Note that, in the case of two-plate imaging, since the fluorescence dispersed by the spectroscopic plate 14 is separately input to each imaging element 13, it is possible to adjust the input of the fluorescence to each imaging element 13 so as not to cause a time difference. For example, by making the distances from the spectroscopic plate 14 to the respective imaging elements 13 the same, it is possible to adjust the input of the fluorescence to each imaging element 13 so as not to cause a time difference. Therefore, the imaging unit 5123 can simultaneously acquire medical images captured with fluorescence having different wavelengths. Therefore, the imaging unit 5123 can simultaneously supply medical images acquired by different imaging elements 13 to an external information processing apparatus.

Here, wavelengths to be transmitted by the filter A and the filter B will be described with reference to FIG. 6. In FIG. 6, the vertical axis represents fluorescence intensity, and the horizontal axis represents wavelength. In FIG. 6, a value obtained by multiplying the spectral intensity of fluorescence to be transmitted by each filter by the characteristic of each filter is plotted. The short wavelength to be transmitted by the filter A is a wavelength for a wider wavelength band including a band of a long wavelength among fluorescence having different wavelengths. On the other hand, the long wavelength to be transmitted by the filter B is a wavelength for a band of a longer wavelength among fluorescence having different wavelengths. In FA1 of FIG. 6, fluorescence having a wavelength of about 800 nm to 1000 nm enters the filter A and the filter B. This wavelength shall have a maximum fluorescence intensity at about 850 nm. Among them, the wavelength to be transmitted by the filter A is a wavelength longer than 808 nm. The band of this wavelength is the entire wavelength of the incident fluorescence. Therefore, the wavelength to be transmitted by the filter A is the same as the wavelength FA11 indicating the entire region. The wavelength to be transmitted by the filter B is longer than 875 nm. As described above, the filter A is desirably a filter having sensitivity on a shorter wavelength side than the filter B. The filter A may be a filter that transmits a wavelength in any band as long as the filter A has sensitivity on a shorter wavelength side than the filter B. The same applies to the cases of FA2 and FA3 in FIG. 6, and thus, the description thereof is appropriately omitted. Here, in FA3 of FIG. 6, the wavelength to be transmitted by the filter A is a wavelength longer than 875 nm, and is not the same as the wavelength FA11 indicating the entire region. Thus, three plots are shown in FA3 of FIG. 6. The three plots are the wavelength FA11 indicating the entire region, the wavelength to be transmitted by the filter A, and the wavelength to be transmitted by the filter B. In FA3 of FIG. 6, since the wavelength to be transmitted by the filter A is longer than 875 nm, the wavelength of 850 nm at which the fluorescence intensity is maximized is not included in any of the wavelength to be transmitted by the filter A and the wavelength to be transmitted by the filter B.

Hereinafter, a process in which the medical image generation apparatus 100 generates an output image with low scattering and low noise on the basis of the degrees of scattering of medical images captured with fluorescence having different wavelengths will be described.

3. Example of Information Processing

3-1. Medical Image Generation Apparatus

Figure 7:
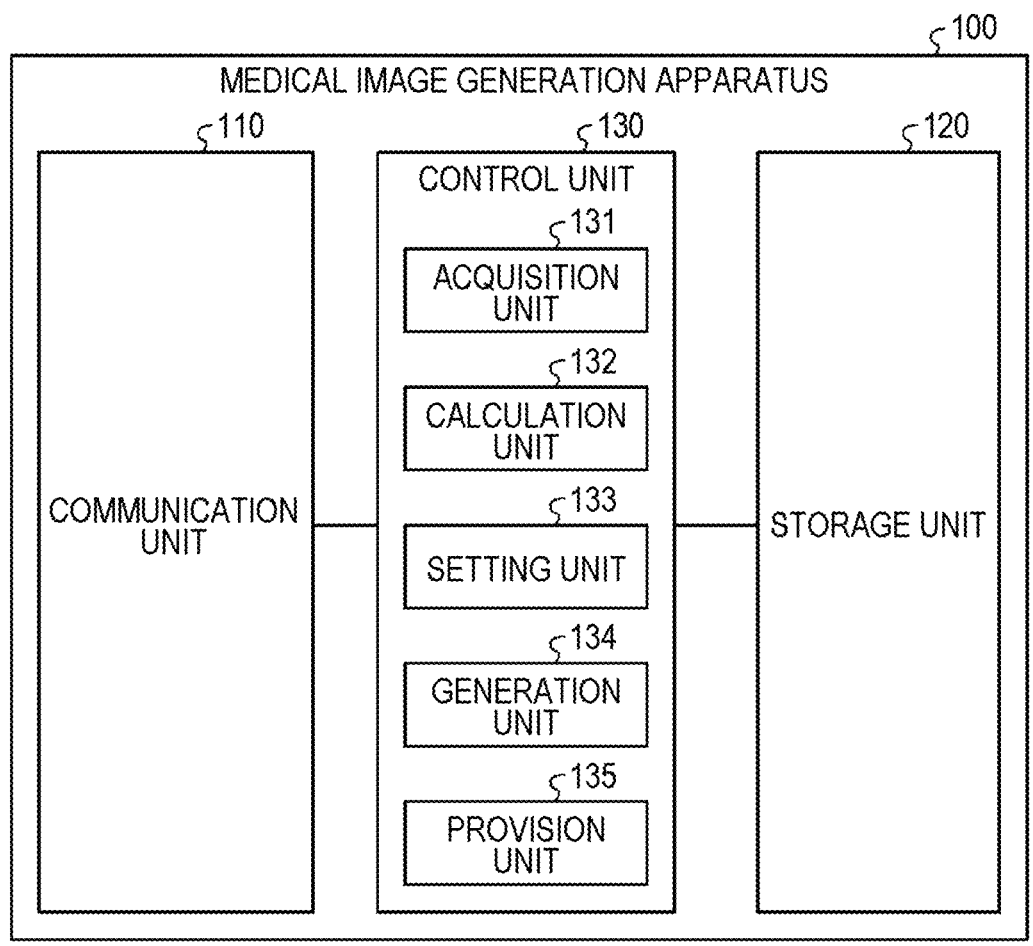
FIG. 7 is a diagram illustrating a configuration example of a medical image generation apparatus according to the embodiment.

Next, the medical image generation apparatus 100 according to the embodiment will be described with reference to FIG. 7. FIG. 7 is a diagram illustrating an example of the medical image generation apparatus 100 according to the embodiment. As illustrated in FIG. 7, the medical image generation apparatus 100 is a computer including a communication unit 110, a storage unit 120, and a control unit 130.

The communication unit 110 is implemented by, for example, a network interface card (NIC) or the like. The communication unit 110 is connected to a network N (not illustrated) in a wired or wireless manner to transmit and receives information to and from the camera head 5119 and the like via the network N. The control unit 130 described later transmits and receives information to and from these devices via the communication unit 110.

The storage unit 120 is implemented by, for example, a semiconductor memory element such as a random access memory (RAM) or a flash memory, or a storage device such as a hard disk or an optical disk. The storage unit 120 stores the medical image transmitted from the imaging unit 5123.

In addition, the storage unit 120 stores the output image generated by the control unit 130. Details of the output image will be described later.

The control unit 130 is implemented, for example, by a central processing unit (CPU) or a micro processing unit (MPU) executing a program (an example of a medical image generation program) stored inside the medical image generation apparatus 100 using a RAM or the like as a work area. Furthermore, the control unit 130 may be implemented by, for example, an integrated circuit such as an application specific integrated circuit (ASIC) or a field programmable gate array (FPGA).

As illustrated in FIG. 7, the control unit 130 includes an acquisition unit 131, a calculation unit 132, a setting unit 133, a generation unit 134, and a provision unit 135, and implements or executes a function and an action of information processing described below. Note that the internal configuration of the control unit 130 is not limited to the configuration illustrated in FIG. 7, and may be another configuration as long as information processing to be described later is performed.

The acquisition unit 131 acquires the medical image transmitted from the imaging unit 5123 via the communication unit 110. Specifically, the acquisition unit 131 acquires a plurality of medical images captured with fluorescence having different wavelengths. Here, characteristics of medical images captured with fluorescence having different wavelengths will be described. In order to describe the characteristics of medical images captured with fluorescence having different wavelengths, the relationship between the wavelength and the fluorescence intensity will be described with reference to FIG. 8.

Figures 8, 9:
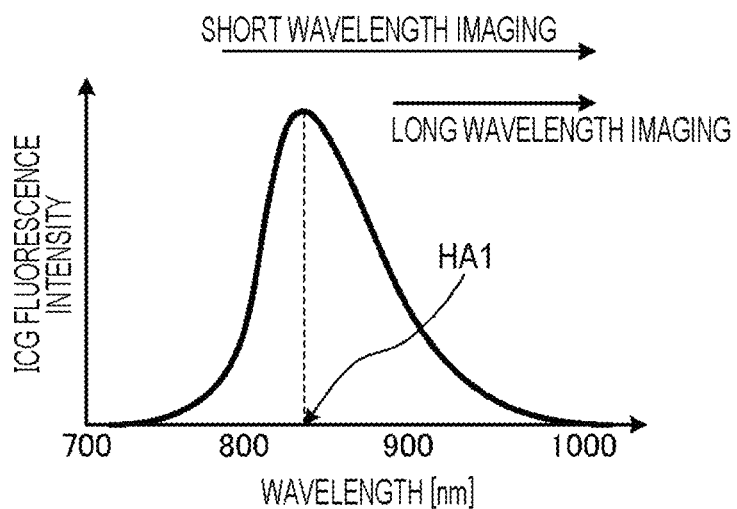
FIG. 8 is a diagram illustrating a relationship between a wavelength and fluorescence intensity according to the embodiment.
FIG. 9 is a diagram illustrating characteristics of medical images captured with fluorescence having different wavelengths according to the embodiment.

FIG. 8 illustrates a relationship between the wavelength and the fluorescence intensity. In FIG. 8, the vertical axis represents fluorescence intensity, and the horizontal axis represents a wavelength. In FIG. 8, the relationship between the fluorescence intensity and the wavelength is plotted. As illustrated in FIG. 8, the fluorescence intensity is maximized at a wavelength HA1. Specifically, the fluorescence intensity is maximized at the wavelength HA1 between 800 nm and 900 nm. Then, at a wavelength equal to or longer than the wavelength at which the fluorescence intensity is maximized, the fluorescence intensity decreases as the wavelength increases. In the embodiment, the acquisition unit 131 acquires a medical image captured with a long wavelength and a medical image captured with a short wavelength as medical images captured with fluorescence having different wavelengths. In FIG. 8, rather than the long wavelength, the short wavelength is for the band of the wavelength at which the fluorescence intensity is higher. In this case, a medical image captured with short wavelength fluorescence is brighter than a medical image captured with long wavelength fluorescence. That is, the medical image captured with a short wavelength has a larger degree of scattering. Note that the calculation of the degree of scattering is performed by the calculation unit 132 as described later. In this case, the acquisition unit 131 acquires a medical image captured with a short wavelength and having a large degree of scattering and a medical image captured with a long wavelength and having a small degree of scattering.

FIG. 9 illustrates characteristics of a medical image captured with long wavelength fluorescence and a medical image captured with short wavelength fluorescence. Here, a characteristic of increasing the visibility of the medical image is an advantage, and a characteristic of decreasing the visibility of the medical image is a disadvantage. As illustrated in FIG. 9, a medical image captured with short wavelength fluorescence has a merit that noise is reduced, but has a demerit that a degree of scattering is increased. On the other hand, a medical image captured with long wavelength fluorescence has a merit that the degree of scattering decreases, but has a demerit that noise increases.

Figure 10:
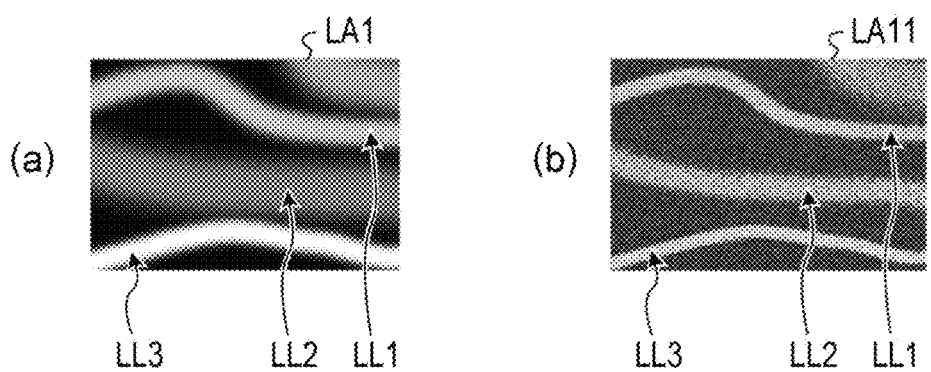
FIG. 10 is a diagram illustrating an example of medical images captured with fluorescence having different wavelengths according to the embodiment.

FIG. 10 illustrates a medical image in which a living body such as a blood vessel appears. With reference to FIG. 10, medical images captured with fluorescence having different wavelengths will be described. FIG. 10(*a*) illustrates a medical image LA1 captured with short wavelength fluorescence. In FIG. 10(*a*), since the degree of scattering of fluorescence of the medical image is large, for example, the living body LL1, the living body LL2, and the like appearing in the medical image LA1 are blurred. Here, the "blur" according to the embodiment will be described. When the feature amount of the predetermined region included in the medical image can be mapped to one pixel of the medical image, it is assumed that there is no blur. In addition, in a case where the feature amount of the predetermined region included in the medical image is required to be mapped to a plurality of pixels of the medical image, the feature amount that is expressed by one pixel is expressed by a plurality of pixels, and thus the image of the feature amount is blurred. This spreading is referred to as blur. As the number of pixels for expressing the feature amount of the predetermined region included in the medical image is larger, the medical image is blurred. Therefore, there is room for further improvement in order to improve the visibility of the medical image. On the other hand, FIG. 10(*b*) illustrates a medical image LA11 captured with long wavelength fluorescence. A medical image LA11 illustrated in FIG. 10(*b*) is a medical image showing a region of the living body same as that of the medical image LA1 illustrated in FIG. 10(*a*). In FIG. 10(*b*), since the degree of scattering of fluorescence of the medical image is small, the living body LL1, the living body LL2, and the like appearing in the medical image LA11 are not blurred (that is, it is clear), but noise increases in the medical image. Therefore, also in FIG. 10(*b*), there is room for further improvement in order to improve the visibility of the medical image.

The calculation unit 132 calculates the degree of scattering of each of medical images obtained by imaging different wavelengths of fluorescence acquired by the acquisition unit 131. This degree of scattering is calculated by a blur width indicating a degree of blur of a living body appearing in the medical image. Here, the blur width indicates the degree of blur from the reference medical image with the medical image in which the living body is not blurred as a reference. The blur width is calculated by the calculation unit 132 on the basis of a difference between the feature amount of the reference medical image and the feature amount of the target medical image. Note that, in the embodiment, the feature amount of the medical image is a feature amount for calculating information regarding the blur width. Hereinafter, calculation of the degree of scattering on the basis of the blur width will be described with reference to FIGS. 11 and 12.

Figure 11:
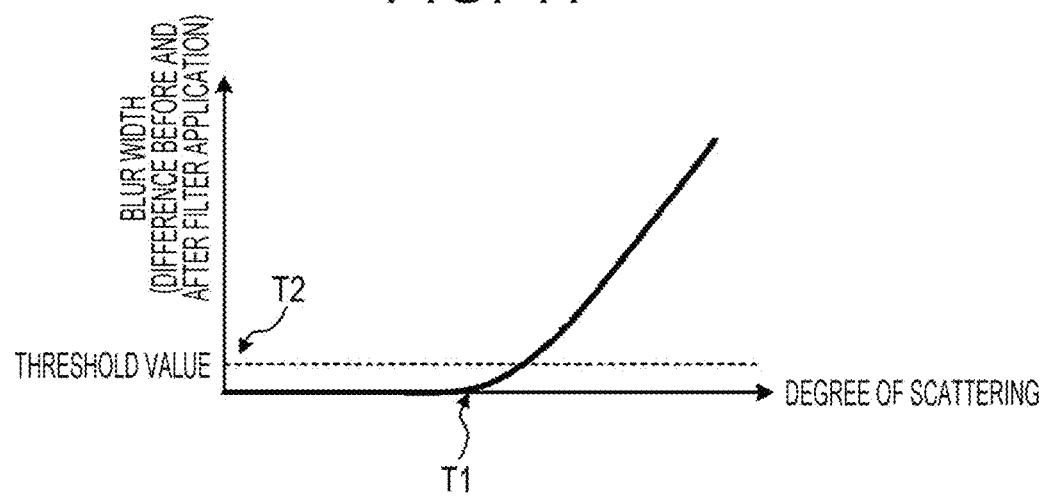
FIG. 11 is a diagram illustrating a relationship between a degree of scattering and a blur width according to the embodiment.

FIG. 11 illustrates a relationship between the blur width and the degree of scattering. The blur width illustrated in FIG. 11 is a difference before and after application of a filter to a medical image. In FIG. 11, the vertical axis represents the blur width (difference before and after filter application), and the horizontal axis represents the degree of scattering. The calculation unit 132 calculates the blur width by applying, as a filter for scattering, a weak filter for scattering small to a strong filter for scattering large to the medical image. Here, in the calculation unit 132, the blur width is highly likely not to change even in a case where a weak filter is applied to a medical image with a large blur. As described above, in the calculation unit 132, the blur width does not change unless a stronger filter is applied to a medical image with a larger blur. The calculation unit 132 calculates the degree of scattering on the basis of the changed degree of blur width. Furthermore, the calculation unit 132 may calculate the degree of scattering on the basis of the relationship between the rank of the strength of the filter to be applied and the degree of scattering. For example, in a case where the blur width changes by the filter of "1" having the weakest rank of the filter strength, the calculation unit 132 sets the degree of scattering to the degree of scattering corresponding to the filter. As illustrated in FIG. 11, as the degree of scattering is increased, the blur width starts to increase in a case where the degree of scattering exceeds T1. The calculation unit 132 calculates the degree of scattering on the basis of the blur width. For example, the imaging unit 5123 can generate medical images having different blur widths by using the plurality of filters 12 having different wavelengths of fluorescence to be transmitted. In this case, the acquisition unit 131 acquires a plurality of medical images having different blur widths from a medical image having a small blur width to a medical image having a large blur width. Then, the calculation unit 132 calculates the degree of scattering on the basis of the blur width of the medical image generated by using the plurality of filters 12. In addition, the generation unit 134 to be described later may use a medical image in which the blur width is equal to or larger than a predetermined threshold value T2 as a medical image having a large degree of scattering for generation of an output image. Note that the predetermined threshold value T2 is calculated by the calculation unit 132 on the basis of the image quality such as noise of the medical image.

Figure 12:
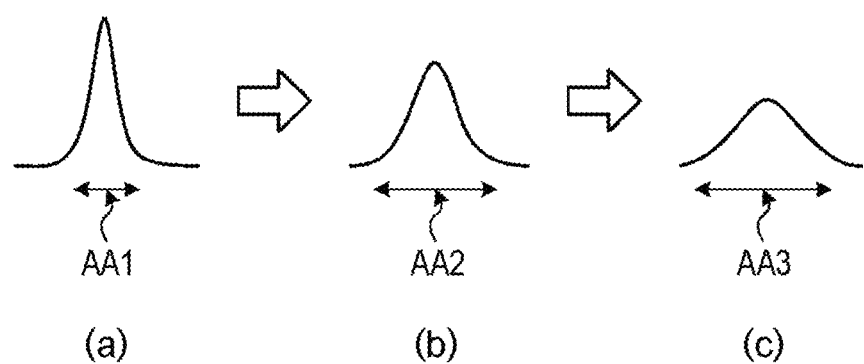
FIG. 12 is a diagram illustrating a relationship between a degree of scattering and a blur width according to the embodiment.

FIG. 12 illustrates a relationship between the blur width and the degree of scattering. FIG. 12 shows that the degree of scattering increases as the blur width increases. FIG. 12(*a*) illustrates a width AA1 of the degree of scattering as a reference for calculating the blur width. That is, in FIG. 12(*a*), the blur width is 0. The calculation unit 132 calculates the degree of scattering of the blurred medical image using AA1. In FIG. 12(*b*), the calculation unit 132 calculates the degree of scattering of the target medical image on the basis of the blur width calculated by "AA2–AA1". In FIG. 12(*c*), the calculation unit 132 calculates the degree of scattering of the target medical image on the basis of the blur width calculated by "AA3–AA1".

Figure 13:
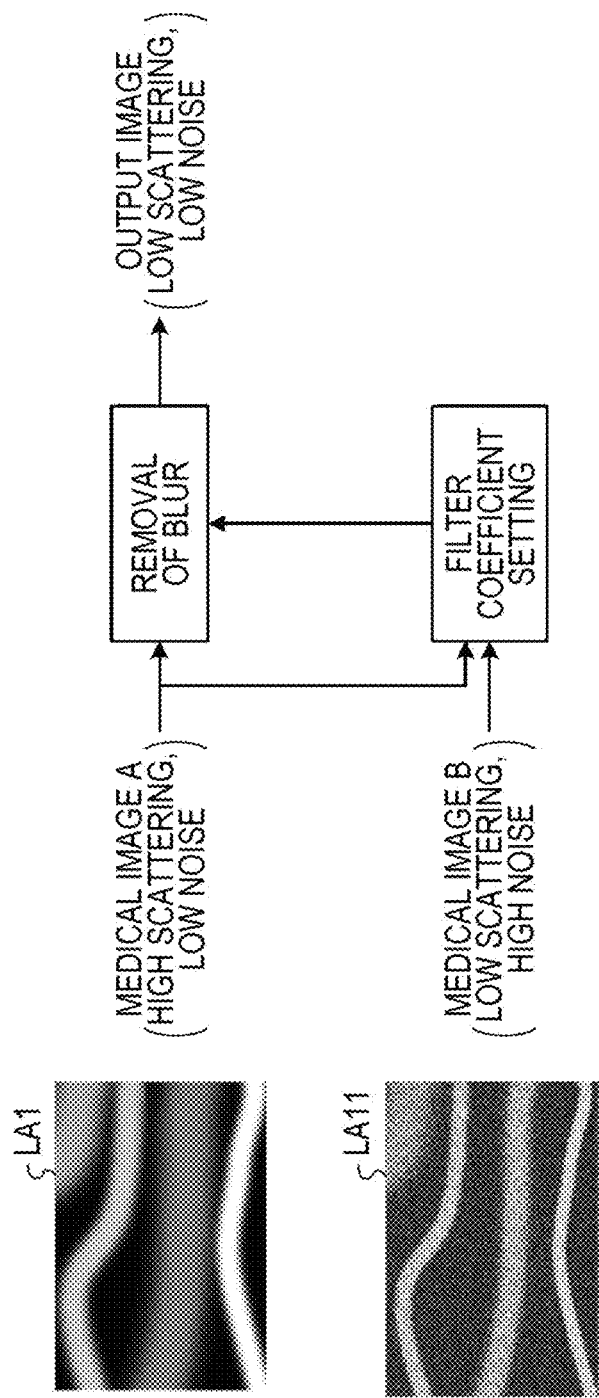
FIG. 13 is a diagram illustrating an example of information processing according to the embodiment.

FIG. 13 illustrates a case where an output image is generated on the basis of a plurality of medical images. In FIG. 13, the output image is generated by removing the blur of the medical image A by applying the filter coefficient to the target medical image by setting the filter coefficient. The setting of the filter coefficient will be described below.

Figure 14:
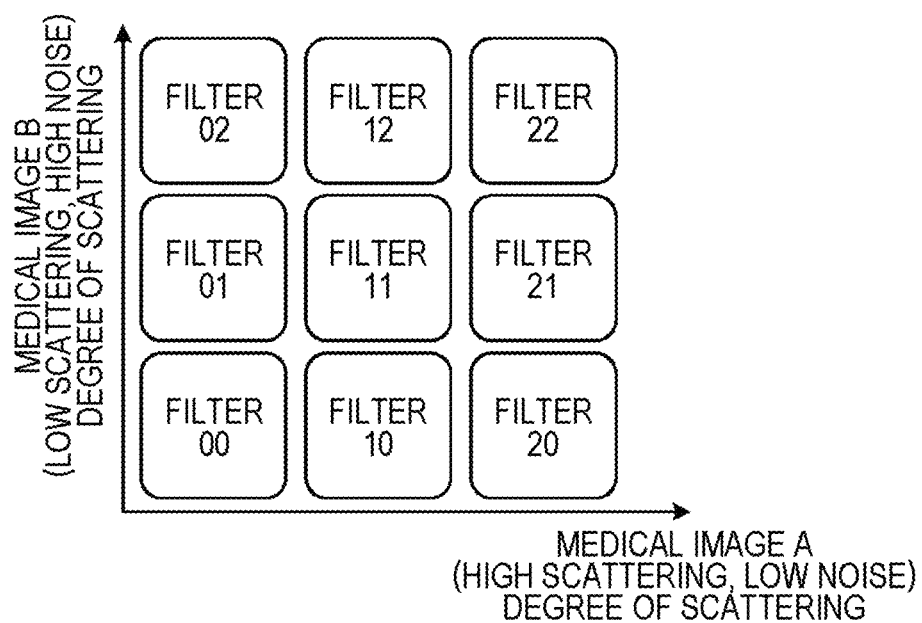
FIG. 14 is a diagram illustrating a relationship between a degree of scattering and a filter coefficient according to the embodiment.

FIG. 14 illustrates a relationship between the degree of scattering of the medical image and the filter. In FIG. 14, the vertical axis represents the degree of scattering of the medical image B, and the horizontal axis represents the degree of scattering of the medical image A. In FIG. 14, a coefficient (hereinafter, appropriately referred to as a "filter coefficient") to be applied to a target medical image is determined on the basis of a combination of a degree of scattering of the medical image A and a degree of scattering of the medical image B. For example, in a case where the degree of scattering of the medical image A is small and the degree of scattering of the medical image B is large, the filter coefficient 02 and the like are determined. In addition, in a case where the degree of scattering of the medical image A is large and the degree of scattering of the medical image B is small, the filter coefficient 20 or the like is determined. The setting unit 133 sets a filter coefficient to be applied to a target medical image on the basis of the combination of the degrees of scattering of the medical images calculated by the calculation unit 132 and the information indicating the relationship between the degree of scattering of the medical image and the filter. In the example of FIG. 14, the setting unit 133 sets the filter coefficient 02, for example, in a case where the degree of scattering of the medical image A is small and the degree of scattering of the medical image B is large. Furthermore, in a case where the degree of scattering of the medical image A is large and the degree of scattering of the medical image B is small, the setting unit 133 sets the filter coefficient 20, for example.

The setting unit 133 sets, by applying to one of the medical images on the basis of the degrees of scattering of the plurality of medical images calculated by the calculation unit 132, a filter coefficient for reproducing a degree of scattering different from the degree of scattering of the one medical image. Then, the generation unit 134 generates an output image on the basis of a difference between the degree of scattering of the medical image having a large degree of scattering and the degree of scattering of the medical image having a small degree of scattering.

The generation unit 134 generates an output image on the basis of the filter coefficient set by the setting unit 133 and the feature amount of the medical image having a large degree of scattering. As a result, the generation unit 134 can generate an output image having a small degree of scattering and less noise. Specifically, since the LA11 is obtained by reducing the blur of LA1 and a filter coefficient for making the blur of the LA1 the blur of the LA11 is set by the setting unit 133, the generation unit 134 applies the filter coefficient to the LA1, so that it is possible to appropriately remove the blur of the LA1. As a result, the generation unit 134 can generate an output image having both advantages of combining the low noise feature among the features of LA1 that are high scattering and low noise and the low scattering feature among the features of LA11 that are low scattering and high noise. As a result, the generation unit 134 can generate a medical image with high visibility.

Figure 15:
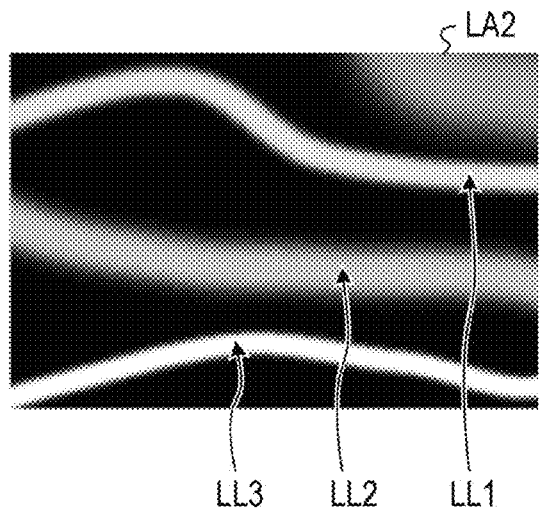
FIG. 15 is a diagram illustrating an example of an output image according to the embodiment.

FIG. 15 illustrates an example of an output image generated by generation unit 134. The output image LA2 illustrated in FIG. 15 is an output image showing a region of the living body same as that of the medical image LA1 or the medical image LA11 illustrated in FIG. 10. Since the output image LA2 has a small degree of scattering of fluorescence, for example, the living body LL1, the living body LL2, and the like appearing in the output image LA2 do not blur. Furthermore, in the output image LA2, the output image has less noise. As a result, the generation unit 134 can generate a medical image with high visibility in fluorescence observation.

The provision unit 135 supplies the output image generated by the generation unit 134 to the display device 5155. The display device 5155 displays the output image supplied from the provision unit 135 in real time. Therefore, the user can observe the output image supplied from the provision unit 135 in real time via the display device 5155.

3-2. Processing Procedure

Figure 16:
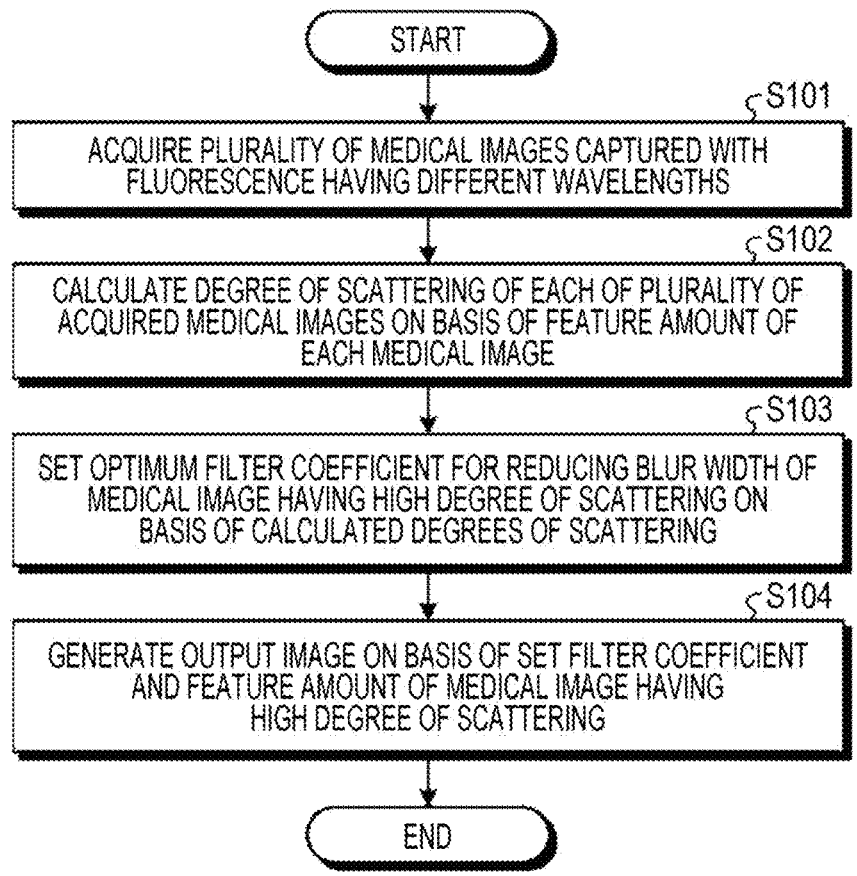
FIG. 16 is a flowchart illustrating a processing procedure according to the embodiment.

Next, a processing procedure according to the embodiment will be described with reference to FIG. 16. FIG. 16 is a flowchart illustrating a processing procedure according to the embodiment. As illustrated in FIG. 16, the medical image generation apparatus 100 acquires a plurality of medical images captured with fluorescence having different wavelengths (step S101).

In addition, the medical image generation apparatus 100 calculates the degree of scattering of each of the plurality of acquired medical images on the basis of the feature amount of each corresponding medical image (step S102). Subsequently, the medical image generation apparatus 100 sets an optimum filter coefficient for reducing the blur width of the medical image having a large degree of scattering on the basis of the calculated degrees of scattering (step S103). Then, the medical image generation apparatus 100 generates an output image on the basis of the set filter coefficient and the feature amount of the medical image having a large degree of scattering (step S104).

4. Modifications

The medical image generation system 1 according to the above-described embodiment may be implemented in various different modes other than the above-described embodiment. Therefore, other embodiments of the medical image generation system 1 will be described below. Note that description of points similar to those in the above embodiment will be omitted.

4-1. Modification 1: Case of Bringing Degree of Scattering Close

In the example described above, the case where the setting unit 133 sets the filter coefficient on the basis of the relationship between the combination of the degrees of scattering and the filter coefficient is described. Here, the setting unit 133 may set an optimum filter coefficient for reducing the blur width of the medical image having a large degree of scattering on the basis of the degrees of scattering of the plurality of medical images. Note that, in Modification 1, since it is not necessary to obtain an accurate value of the degree of scattering, the degree of scattering of the medical image is not calculated.

4-1-1. Medical Image Generation Apparatus

Figure 17:
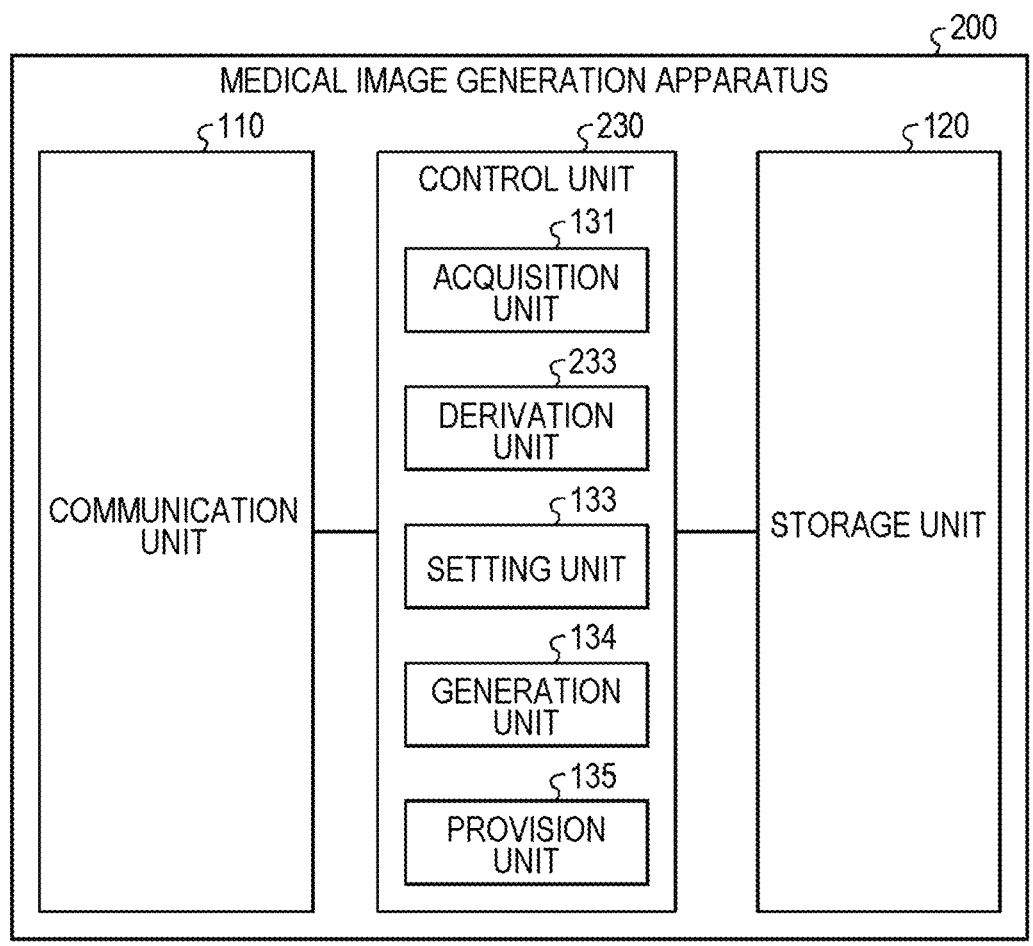
FIG. 17 is a diagram illustrating a configuration example of a medical image generation apparatus according to the embodiment.

Next, a medical image generation apparatus 200 according to Modification 1 will be described with reference to FIG. 17. FIG. 17 is a diagram illustrating an example of the medical image generation apparatus 200 according to Modification 1. As illustrated in FIG. 17, the medical image generation apparatus 200 is a computer including the communication unit 110, the storage unit 120, and a control unit 230. Hereinafter, the description similar to that of the above embodiment will be appropriately omitted.

As illustrated in FIG. 17, the control unit 230 includes the acquisition unit 131, a derivation unit 233, the setting unit 133, the generation unit 134, and the provision unit 135, and implements or executes a function and an action of information processing described below. Note that the internal configuration of the control unit 230 is not limited to the configuration illustrated in FIG. 17, and may be another configuration as long as information processing to be described later is performed.

The derivation unit 233 derives, by applying to one medical image having a degree of scattering on the basis of the degrees of scattering of the plurality of medical images, the filter coefficient for reproducing a degree of scattering of the other medical image. For example, the derivation unit 233 derives an optimum filter coefficient for reproducing the degree of scattering of the medical image having the small degree of scattering among the filter coefficients for reproducing the small degree of scattering in the medical image having the large degree of scattering.

The setting unit 133 sets an optimum filter coefficient for reproducing the degree of scattering of a medical image having a small degree of scattering in a medical image having a large degree of scattering on the basis of the filter coefficient derived by the derivation unit 233.

The generation unit 134 generates an output image on the basis of the filter coefficient set by the setting unit 133 and the feature amount of the medical image having a large degree of scattering.

4-1-2. Generation of Output Image Using Inverse Filter Coefficient

Furthermore, the medical image generation apparatus 200 may set an optimum filter coefficient for reducing the blur width of the medical image having a large degree of scattering by deriving the optimum filter coefficient for reproducing the degree of scattering of the medical image having a large degree of scattering in the medical image having a small degree of scattering.

Figure 18:
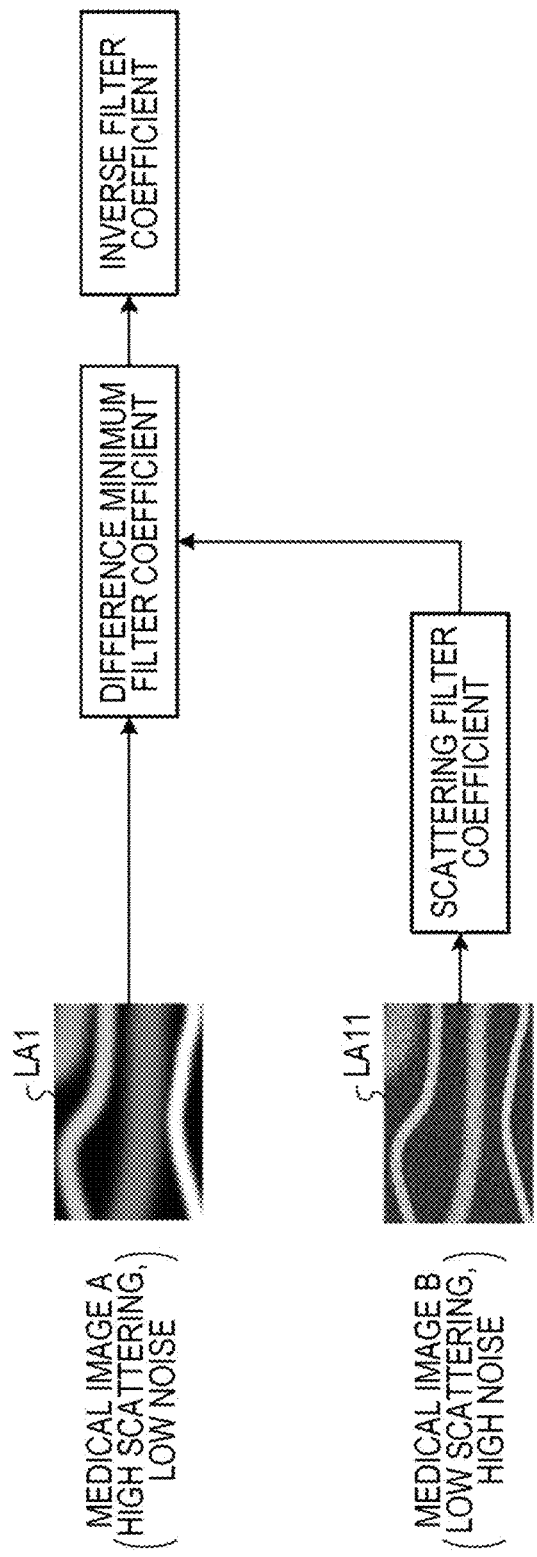
FIG. 18 is a diagram illustrating an example of information processing according to the embodiment.

As illustrated in FIG. 18, the derivation unit 233 derives an optimum filter coefficient (hereinafter, appropriately referred to as a "difference minimum filter coefficient") for reproducing the degree of scattering of the medical image having a large degree of scattering among filter coefficients (hereinafter, appropriately referred to as "scattering filter coefficient") for reproducing a large degree of scattering in the medical image having a small degree of scattering on the basis of the degrees of scattering of the plurality of medical images. That is, in FIG. 18, the derivation unit 233 derives the difference minimum filter coefficient that minimizes the difference between a degree of scattering of the medical image having a large degree of scattering and a degree of scattering among the plurality of degrees of scattering reproduced by applying the scattering filter coefficient to the medical image having a small degree of scattering.

The setting unit 133 sets an optimum filter coefficient for reproducing the degree of scattering of the medical image having a small degree of scattering in the medical image having a large degree of scattering on the basis of the difference minimum filter coefficient derived by the derivation unit 233. Such a filter coefficient based on the difference minimum filter coefficient is appropriately referred to as an "inverse filter coefficient".

The generation unit 134 generates an output image on the basis of the inverse filter coefficient set by the setting unit 133 and the feature amount of the medical image having a large degree of scattering.

Figure 19:
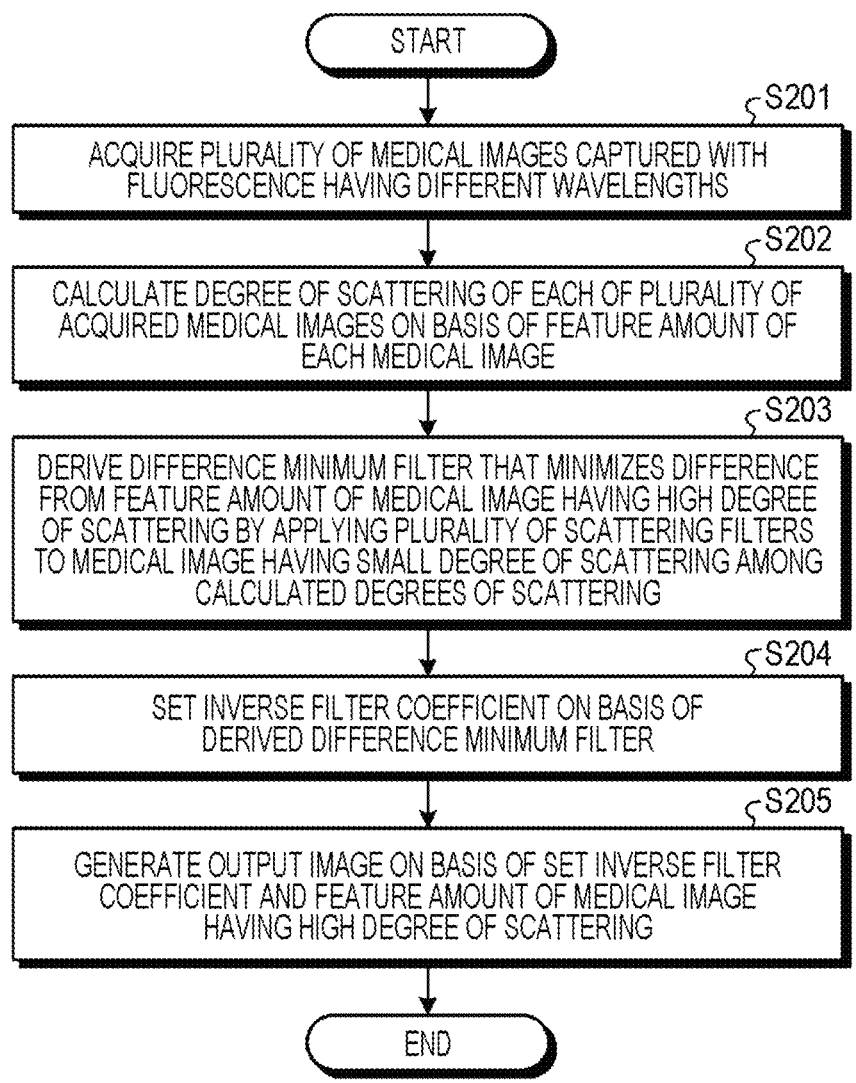
FIG. 19 is a flowchart illustrating a processing procedure according to the embodiment.

Next, a processing procedure according to Modification 1 will be described with reference to FIG. 19. FIG. 19 is a flowchart illustrating a processing procedure according to Modification 1. Steps S201 and 202 are similar to those in the above embodiment, and thus description thereof is omitted.

As illustrated in FIG. 19, the medical image generation apparatus 100 derives a difference minimum filter coefficient that minimizes a difference between a degree of scattering of the medical image having a large degree of scattering and a degree of scattering among a plurality of degrees of scattering reproduced by applying the scattering filter coefficient to the medical image having the small degree of scattering on the basis of the calculated degrees of scattering (step S203). In addition, the medical image generation apparatus 100 sets an inverse filter coefficient on the basis of the derived difference minimum filter (step S204). Then, the medical image generation apparatus 100 generates an output image on the basis of the set inverse filter coefficient and the feature amount of the medical image having a large degree of scattering (step S205).

4-2. Modification 2: Generation of Output Image on the Basis of Difference in Degrees of Scattering In the above-described example, the case where the generation unit 134 generates the output image on the basis of the feature amount of the medical image having a large degree of scattering and the filter coefficient is described. As described above, in the example described above, the generation unit 134 generates the output image using the filter coefficient set by the setting unit 133. Here, a medical image generation apparatus 300 may generate the output image on the basis of a combination ratio that is a ratio for combining a medical image having a large degree of scattering with a medical image having a small degree of scattering. Specifically, the medical image generation apparatus 300 may generate the output image on the basis of a combination ratio according to a difference in degrees of scattering between a medical image having a large degree of scattering and a medical image having a small degree of scattering.

4-2-1. Medical Image Generation Apparatus

Figure 20:
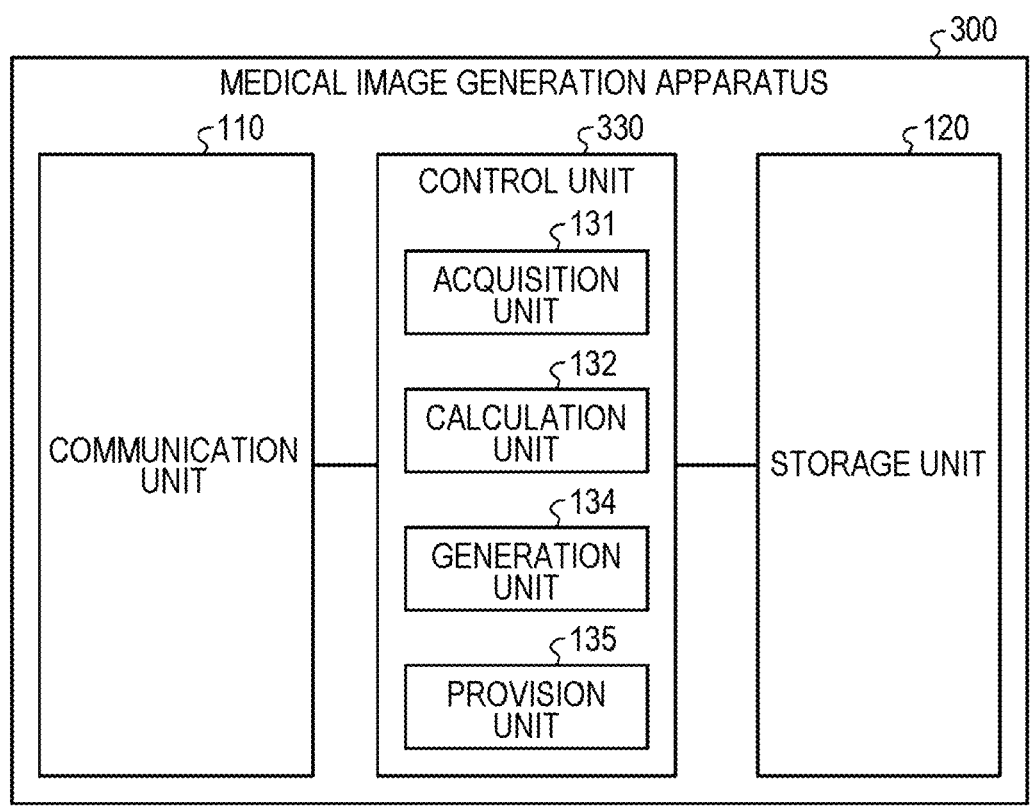
FIG. 20 is a diagram illustrating a configuration example of a medical image generation apparatus according to the embodiment.

Next, a medical image generation apparatus 300 according to Modification 2 will be described with reference to FIG. 20. FIG. 20 is a diagram illustrating an example of the medical image generation apparatus 300 according to Modification 2. As illustrated in FIG. 20, the medical image generation apparatus 300 is a computer including the communication unit 110, the storage unit 120, and a control unit 330. Hereinafter, the description similar to that of the above embodiment will be appropriately omitted.

As illustrated in FIG. 20, the control unit 330 includes the acquisition unit 131, the calculation unit 132, the generation unit 134, and the provision unit 135, and implements or executes a function and an action of information processing described below. Note that the medical image generation apparatus 300 may not include the setting unit 133. Note that the internal configuration of the control unit 330 is not limited to the configuration illustrated in FIG. 20, and may be another configuration as long as information processing to be described later is performed.

Figure 21:
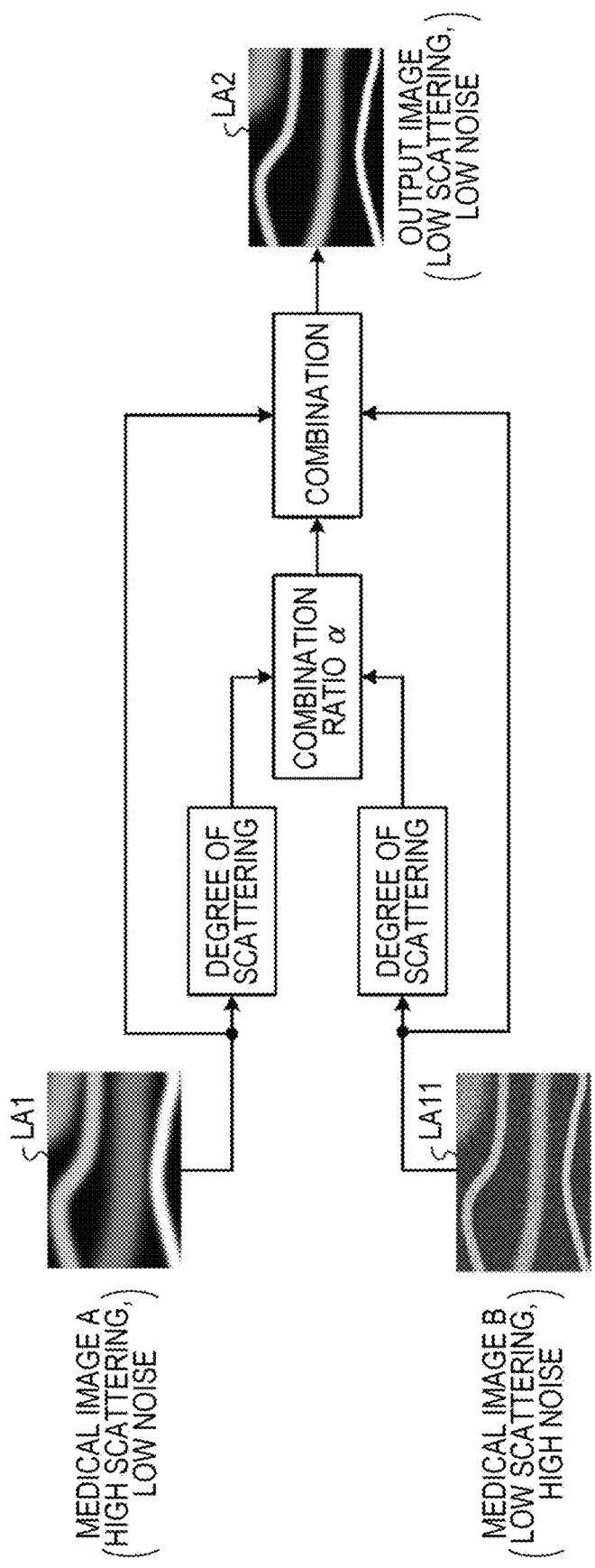
FIG. 21 is a diagram illustrating an example of information processing according to the embodiment.

FIG. 21 is a diagram for describing information processing performed by the calculation unit 132 and the generation unit 134. The calculation unit 132 calculates a difference in degrees of scattering between a medical image having a large degree of scattering and a medical image having a small degree of scattering. Then, the calculation unit 132 calculates the combination ratio on the basis of the difference in degrees of scattering and the information indicating the relationship between the combination ratio and the difference in degrees of scattering.

Figure 22:
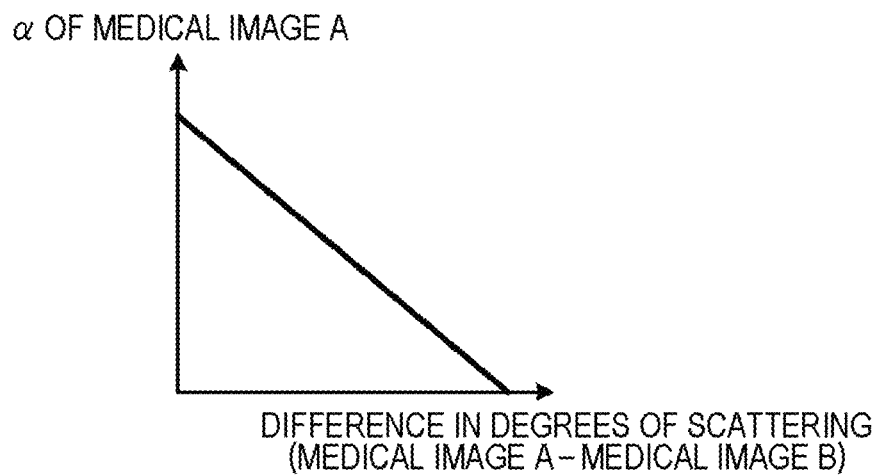
FIG. 22 is a diagram illustrating a relationship between a difference in degrees of scattering and a combination ratio according to the embodiment.

FIG. 22 illustrates an example of information indicating the relationship between the combination ratio and the difference in degrees of scattering. In FIG. 22, the vertical axis represents the combination ratio of the medical image A, and the horizontal axis represents the difference in degrees of scattering between the medical image A and the medical image B. Note that, in FIG. 22, the medical image A is an example of a medical image having a large degree of scattering, and the medical image B is an example of a medical image having a small degree of scattering. In FIG. 21, the combination ratio of the medical image A is plotted according to the difference in degrees of scattering between the medical image A and the medical image B. The calculation unit 132 calculates the combination ratio of the plurality of target medical images by comparing the difference in degrees of scattering between the plurality of medical images with information indicating the relationship between the combination ratio and the difference in degrees of scattering.

Furthermore, the calculation unit 132 may calculate the combination ratio using the learning model M2 generated by learning the relationship between the combination ratio and the difference in degrees of scattering. For example, the calculation unit 132 may calculate the combination ratio by using the learning model M2 generated by learning the combination ratio as the output information with the difference in degrees of scattering as the input information. The calculation unit 132 may calculate the combination ratio of the plurality of target medical images by inputting the difference in degrees of scattering between the plurality of target medical images to the learning model M2.

The generation unit 134 generates an output image by combining a medical image having a large degree of scattering with a medical image having a small degree of scattering on the basis of the combination ratio calculated by the calculation unit 132.

4-2-2. Processing Procedure

Figure 23:
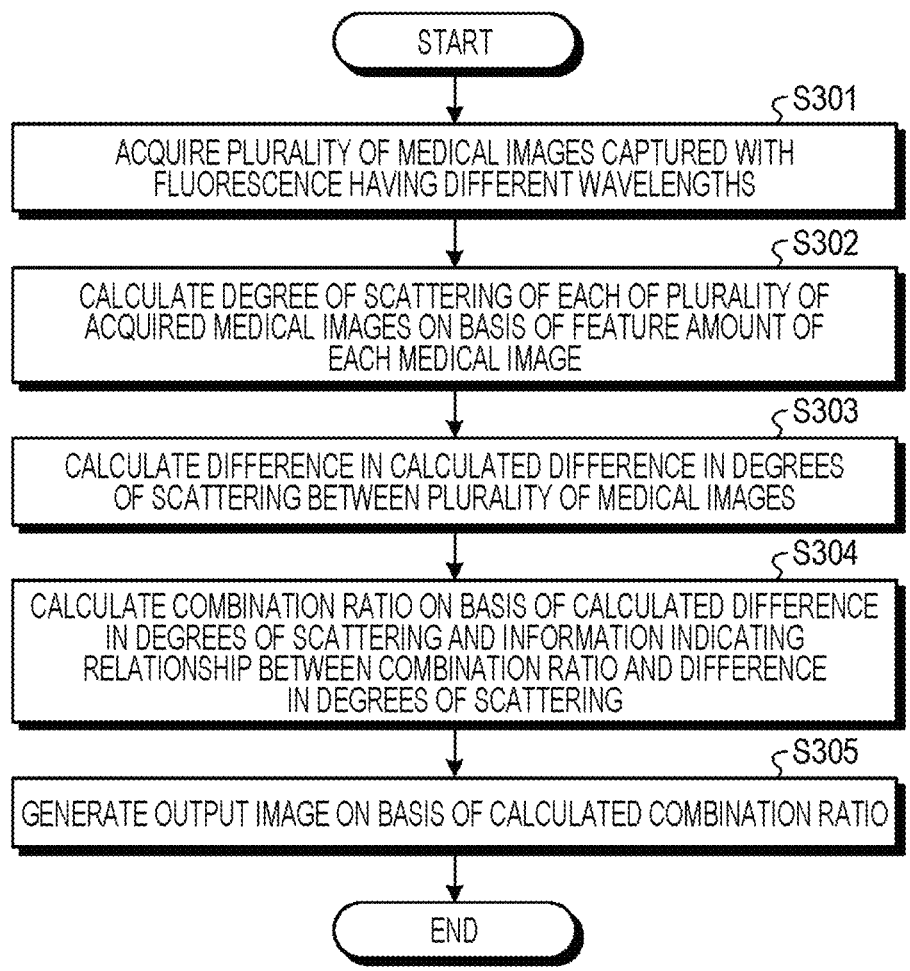
FIG. 23 is a flowchart illustrating a processing procedure according to the embodiment.

Next, a processing procedure according to Modification 2 will be described with reference to FIG. 23. FIG. 23 is a flowchart illustrating a processing procedure according to Modification 2. Steps S301 and 302 are the same as those in the above embodiment, and thus description thereof is omitted.

As illustrated in FIG. 23, the medical image generation apparatus 100 calculates a difference between the calculated degrees of scattering of the plurality of medical images (step S303). In addition, the medical image generation apparatus 100 calculates the combination ratio on the basis of the calculated difference in degrees of scattering and the information indicating the relationship between the combination ratio and the difference in degrees of scattering (step S304). Then, the medical image generation apparatus 100 generates an output image on the basis of the calculated combination ratio (step S305).

4-3. Modification 3: Visualization of Scattering Suppression Effect in Output Image The above-described example shows a case where the generation unit 134 generates an output image with low scattering and low noise. Therefore, the generation unit 134 can generate an output image with high visibility of fluorescence in the deep part of the living body in fluorescence observation. However, in the above-described example, the possibility that the sense of depth of the output image is reduced by suppressing the scattering of the fluorescence cannot be denied. Hereinafter, information processing in which a medical image generation apparatus 400 can improve a sense of depth of an output image by adding information for displaying, in a visible state, an effect (hereinafter, appropriately referred to as a "scattering suppression effect") in which scattering of fluorescence is suppressed will be described.

4-3-1. Medical Image Generation Apparatus

Figure 24:
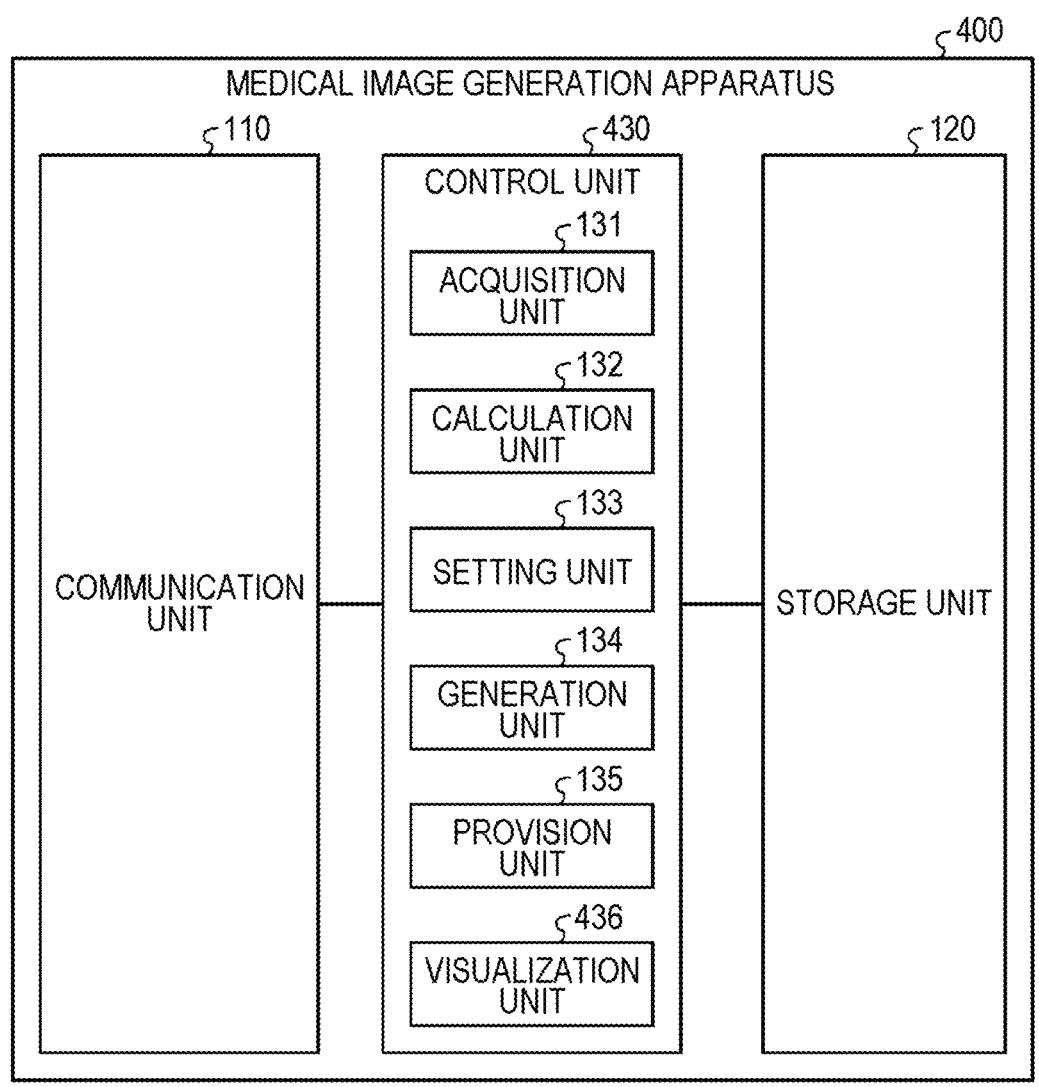
FIG. 24 is a diagram illustrating a configuration example of a medical image generation apparatus according to the embodiment.

Next, the medical image generation apparatus 400 according to Modification 3 will be described with reference to FIG. 24. FIG. 24 is a diagram illustrating an example of the medical image generation apparatus 400 according to Modification 3. As illustrated in FIG. 24, the medical image generation apparatus 400 is a computer including the communication unit 110, the storage unit 120, and a control unit 430. Hereinafter, the description similar to that of the above embodiment will be appropriately omitted.

As illustrated in FIG. 24, the control unit 430 includes the acquisition unit 131, the calculation unit 132, the setting unit 133, the generation unit 134, a visualization unit 435, and the provision unit 135, and implements or executes a function and an action of information processing described below. Note that the internal configuration of the control unit 430 is not limited to the configuration illustrated in FIG. 23, and may be another configuration as long as information processing to be described later is performed.

The calculation unit 132 calculates the scattering suppression effect value indicating the scattering suppression effect by using one of the following two processes.

The calculation unit 132 calculates a difference in degrees of scattering between the plurality of medical images as a scattering suppression effect value.

Figure 25:
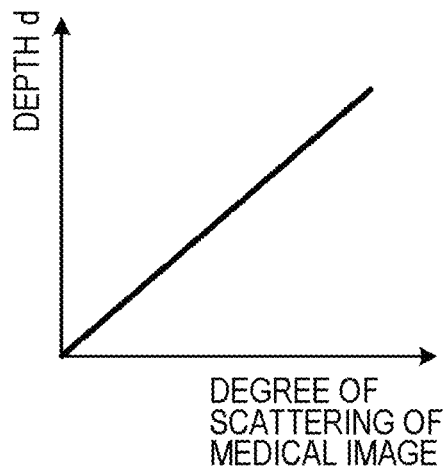
FIG. 25 is a diagram illustrating a relationship between a degree of scattering and a depth according to the embodiment.

FIG. 25 illustrates an example of information indicating the relationship between the degree of scattering of the medical image and the depth at which the medical image is captured. Note that the depth at which the medical image was captured is the depth from the surface of the observation target. In FIG. 25, the vertical axis represents the depth, and the horizontal axis represents the degree of scattering. In FIG. 25, the relationship between the degree of scattering and the depth of the medical image is plotted. The calculation unit 132 calculates the depth of the target medical image by comparing the degree of scattering of the target medical image with information indicating a relationship between the degree of scattering and the depth of the medical image.

Figure 26:
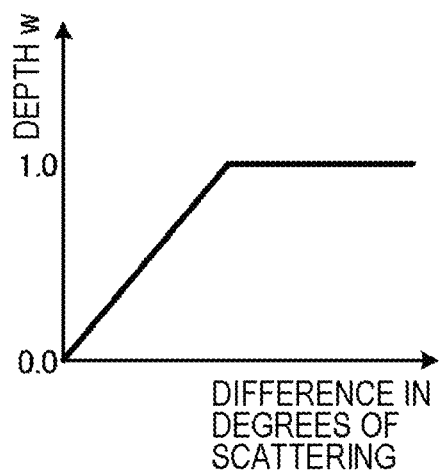
FIG. 26 is a diagram illustrating a relationship between a difference in degrees of scattering and a weight according to the embodiment.

FIG. 26 illustrates an example of information indicating the relationship between the difference in degrees of scattering and the weight for calculating the scattering suppression effect value. In FIG. 26, the vertical axis represents the weight, and the horizontal axis represents the difference in degrees of scattering. In FIG. 26, the weights are plotted according to the difference in degrees of scattering between the medical images. The calculation unit 132 calculates the weight for calculating the scattering suppression effect value by comparing the difference in degrees of scattering between the plurality of target medical images with the information indicating the relationship between the difference in degrees of scattering and the weight.

The calculation unit 132 calculates the scattering suppression effect value by multiplying the depth of the target medical image by the weight for calculating the scattering suppression effect value.

The visualization unit 435 adds information for displaying the scattering suppression effect in a visible state to the output image generated by the generation unit 134 on the basis of the scattering suppression effect value calculated by the calculation unit 132. Here, the information for displaying the scattering suppression effect in a visible state is, for example, color information. The color information may be color information colored with a color map or may be color information colored with a single color.

Figure 27:
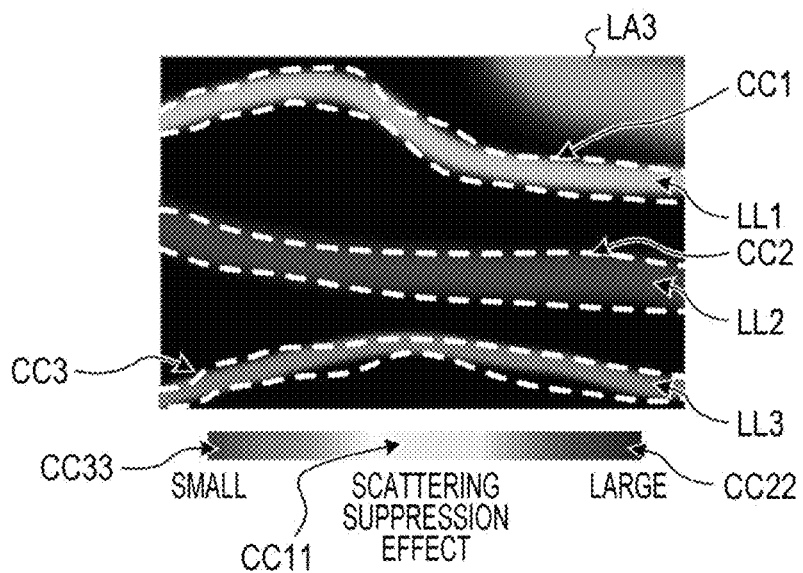
FIG. 27 is a diagram illustrating an example (color map) of an output image showing a scattering suppression effect in a visible state according to the embodiment.

FIG. 27 illustrates an output image LA3 in which the scattering suppression effect is displayed in a visible state using the color map. In FIG. 27, a smaller scattering suppression effect value is colored in red, and a larger scattering suppression effect value is colored in blue. In FIG. 27, a region CC1 surrounding the living body LL1 by a dotted line is colored in CC11 indicating green. In addition, an area CC2 surrounding the living body LL2 with a dotted line is colored in CC22 indicating blue. In addition, an area CC3 surrounding the living body LL3 with a dotted line is colored in CC33 indicating red. Therefore, in the living body appearing in the output image LA3, it can be visually understood that the living body LL2 was not blurred the most and the generation LL3 was blurred the most.

Figure 28:
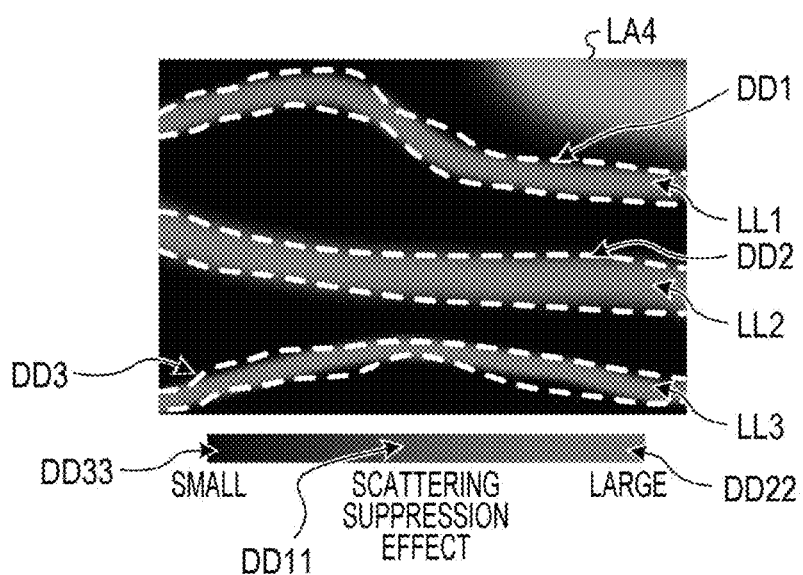
FIG. 28 is a diagram illustrating an example (single color) of an output image showing a scattering suppression effect in a visible state according to the embodiment.

FIG. 28 illustrates an output image LA3 in which the scattering suppression effect is displayed in a visible state using a single color. In FIG. 28, a smaller scattering suppression effect value is colored in a dark color, and a larger scattering suppression effect value is colored in a bright color. In FIG. 28, a region DD1 surrounding the living body LL1 by a dotted line is colored in DD11 indicating an intermediate color between a light color and a dark color. A region DD2 surrounding the living body LL2 with a dotted line is colored in DD22 indicating a light color. A region DD3 surrounding the living body LL3 with a dotted line is colored in DD33 indicating a dark color. Therefore, in the living body appearing in the output image LA3, it can be visually understood that the living body LL2 was not blurred the most and the generation LL3 was blurred the most.

The provision unit 135 supplies to the display device 5155 the output image to which the information for displaying the scattering suppression effect in a visible state is added by the visualization unit 435.

4-3-2. Processing Procedure

Figure 29:
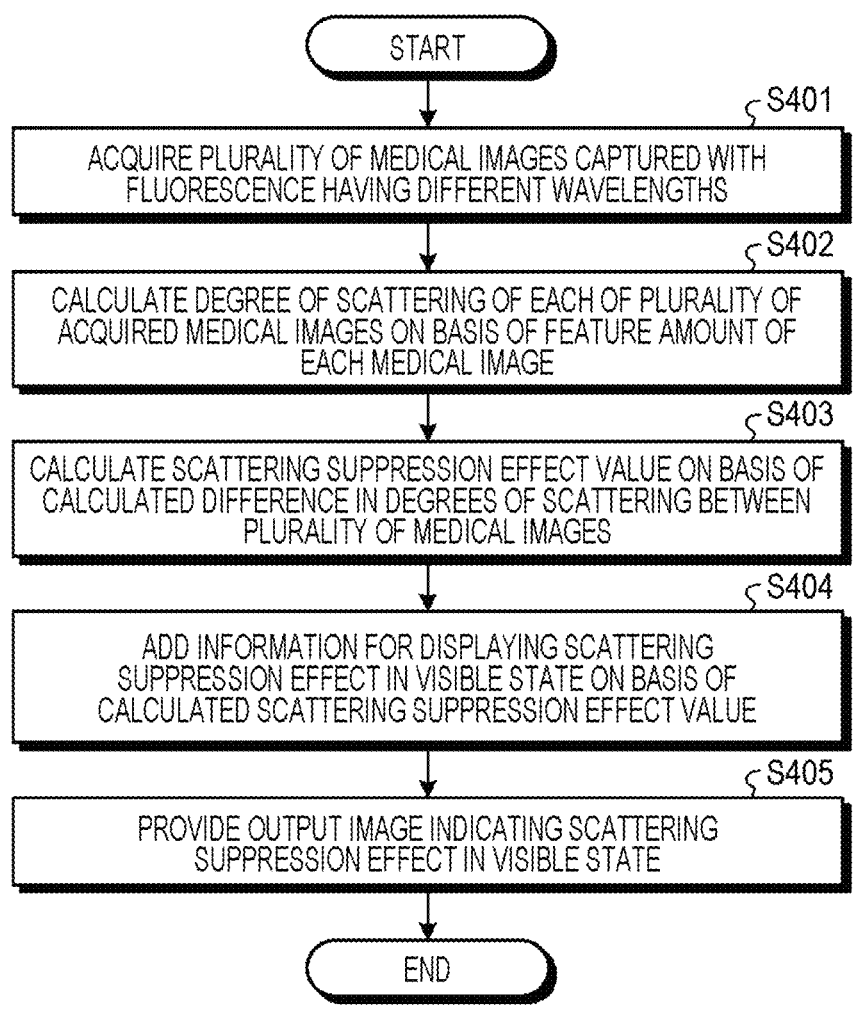
FIG. 29 is a flowchart illustrating a processing procedure according to the embodiment.

Next, a processing procedure according to Modification 3 will be described with reference to FIG. 29. FIG. 29 is a flowchart illustrating a processing procedure according to Modification 3. Steps S401 and 402 are the same as those in the above embodiment, and thus description thereof is omitted.

As illustrated in FIG. 29, the medical image generation apparatus 100 calculates the scattering suppression effect value on the basis of the calculated difference in degrees of scattering between the plurality of medical images (step S403). In addition, the medical image generation apparatus 100 adds information for displaying the scattering suppression effect in a visible state on the basis of the calculated scattering suppression effect value (step S404). Then, the medical image generation apparatus 100 provides an output image indicating the scattering suppression effect in a visible state (step S405).

5. Variations of Processing

5-1. Removal of Blur for Each Region and for Each Pixel

In the above embodiment, the case where the setting unit 133 performs the processing for removing the blur of the medical image on the basis of the degrees of scattering of the plurality of medical images is described. Here, the setting unit 133 may perform the processing for removing the blur of the medical image for each region or each pixel on the basis of the degree of scattering of the medical image for each region or each pixel included in the plurality of medical images. Hereinafter, a specific process for removing the blur for each region by the setting unit 133 will be described as an example, but the same applies to a case where the blur is removed for each pixel. Note that the same description as in the above embodiment will be omitted as appropriate.

The calculation unit 132 calculates the degree of scattering of the medical image for each region included in the plurality of medical images. Specifically, the calculation unit 132 calculates the degree of scattering of the medical image for each region corresponding to an identical position information included in each medical image. Furthermore, the setting unit 133 sets an optimum filter coefficient for each region on the basis of the degree of scattering for each region calculated by the calculation unit 132. As a result, the setting unit 133 can set an optimum filter coefficient for removing the blur of the medical image for each region, so that the blur can be removed with higher accuracy. Then, the generation unit 134 generates the output image by applying the filter coefficient for each region set by the setting unit 133 to the target medical image for each region.

5-2. Information Processing in a Case where Blur Width is Less than Predetermined Threshold Value In the above embodiment, the case where the generation unit 134 uses the medical image in which the blur width is equal to or larger than the predetermined threshold value as the medical image having a large degree of scattering for generation of the output image is described. Here, in a case where the blur width does not exceed the predetermined threshold value even in a case where the filter 12 in which the degree of scattering calculated by the calculation unit 132 is maximized is used, the generation unit 134 may use the medical image to which the filter 12 is applied as the medical image having a large degree of scattering for generation of the output image.

5-3. Calculation of Degree of Scattering Using Learning Model

In the above embodiment, the case where the calculation unit 132 calculates the degree of scattering on the basis of the predetermined relationship between the blur width and the degree of scattering is described. Here, the calculation unit 132 may calculate the degree of scattering using the learning model M1 generated by learning the relationship between the blur width and the degree of scattering. For example, the calculation unit 132 may calculate the degree of scattering by using the learning model M1 generated by learning with the blur width based on the plurality of medical images generated by using the plurality of filters 12 as the input information and the degree of scattering as the output information. As described above, the blur width can be calculated on the basis of the plurality of medical images generated by using the plurality of filters 12. Therefore, the calculation unit 132 may calculate the degree of scattering of the target medical image by inputting the blur width calculated from the plurality of medical images including the target medical image to the learning model M1.

5-4. Fluorescence Example Other than ICG Fluorescence

Figure 30:
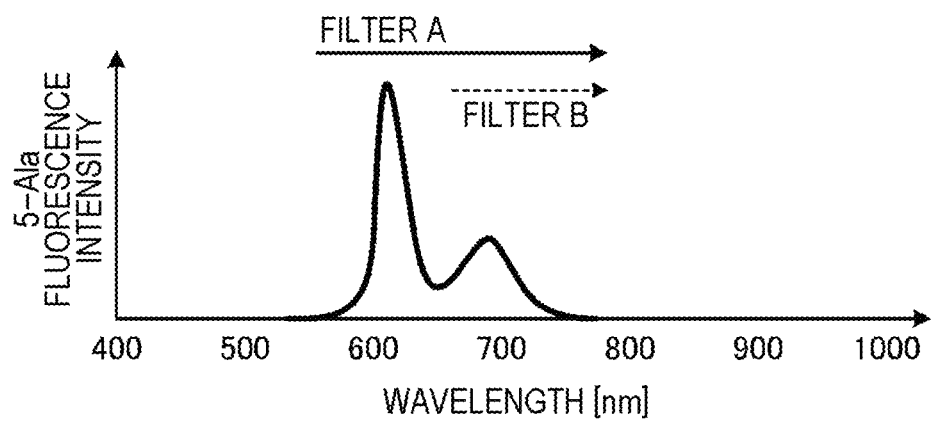
FIG. 30 is a diagram illustrating a relationship (5-Ala) between a wavelength and fluorescence intensity according to the embodiment.
Figure 31:
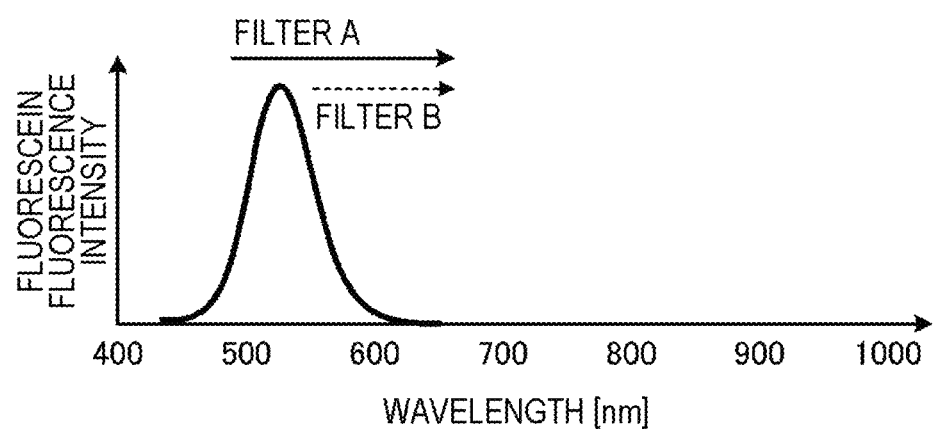
FIG. 31 is a diagram illustrating a relationship (fluorescein) between a wavelength and fluorescence intensity according to the embodiment.

In the above embodiment, an example of information processing used for fluorescence observation by ICG is described, but the present invention is not limited to this example. That is, the fluorescence according to the embodiment is not limited to the fluorescence by ICG, and may be any fluorescence. For example, the fluorescence according to the embodiment may be fluorescence by 5-Ala (PpIX), fluorescein, or the like. FIG. 30 illustrates the relationship between the wavelength and the fluorescence intensity in the case of using 5-Ala (PpIX). As shown in FIG. 30, the fluorescence intensity of 5-Ala (PpIX) peaks around wavelengths of 635 nm and 700 nm. FIG. 31 shows the relationship between the wavelength and the fluorescence intensity in the case of using fluorescein. As shown in FIG. 30, the fluorescence intensity of fluorescein peaks around a wavelength of 520 nm. In FIGS. 30 and 31, as in the case of ICG, the filter A may be a filter that transmits a wavelength in any band as long as the filter A is a filter sensitive to a shorter wavelength side than the filter B.

5-5. Limitation by Spectroscopic Plate

In the above embodiment, the case where the spectroscopic plate 14 reflects fluorescence of a specific wavelength included in the fluorescence to transmit fluorescence of another wavelength, other than the specific wavelength, included in the fluorescence is described. Here, the spectroscopic plate 14 may not reflect fluorescence of a specific wavelength, but may reflect the incident fluorescence itself in two directions toward the filter A and the filter B. In this case, the same fluorescence enters the filter A and the filter B. Then, using the filter A and the filter B, a wavelength for capturing an image by each imaging element may be selected. In this case, the filter A and the filter B each transmit only fluorescence of a desired wavelength.

5-6. Filter Strength

In the above embodiment, the case where the setting unit 133 sets the filter coefficient to be applied to the target medical image is described. In this case, the generation unit 134 generates the output image with less blur by applying the filter coefficient to the feature amount of the medical image. Here, the setting unit 133 may set the strength of the filter to be applied to the target medical image. In this case, the generation unit 134 generates the output image by applying the filter with the intensity set by the setting unit 133 to the target medical image.

6. Hardware Configuration

Figure 32:
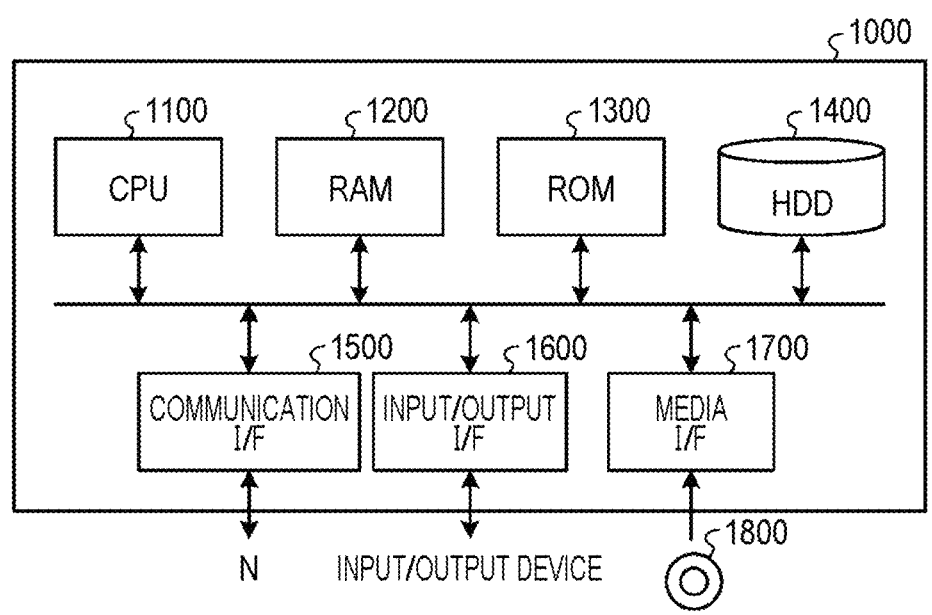
FIG. 32 is a hardware configuration diagram illustrating an example of a computer that implements functions of the medical image generation apparatus.

Furthermore, the medical image generation apparatus 100 (200, 300, 400) and the camera head 5119 according to the above-described embodiments are implemented by, for example, a computer 1000 having a configuration as illustrated in FIG. 32. FIG. 32 is a hardware configuration diagram illustrating an example of a computer that implements the functions of the medical image generation apparatus 100 (200, 300, 400). The computer 1000 includes a CPU 1100, a RAM 1200, a ROM 1300, an HDD 1400, a communication interface (I/F) 1500, an input/output interface (I/F) 1600, and a media interface (I/F) 1700.

The CPU 1100 operates on the basis of a program stored in the ROM 1300 or the HDD 1400, and controls each unit. The ROM 1300 stores a boot program executed by the CPU 1100 when the computer 1000 is activated, a program depending on hardware of the computer 1000, and the like.

The HDD 1400 stores a program executed by the CPU 1100, data used by the program, and the like. The communication interface 1500 receives data from another device via a predetermined communication network to transmit the data to the CPU 1100 to transmit data generated by the CPU 1100 to another device via a predetermined communication network.

The CPU 1100 controls output devices such as a display and a printer and input devices such as a keyboard and a mouse via the input/output interface 1600. The CPU 1100 acquires data from the input device via the input/output interface 1600. In addition, the CPU 1100 outputs the generated data to the output device via the input/output interface 1600.

The media interface 1700 reads a program or data stored in a recording medium 1800 and provides the program or data to the CPU 1100 via the RAM 1200. The CPU 1100 loads the program from the recording medium 1800 onto the RAM 1200 via the media interface 1700, and executes the loaded program. The recording medium 1800 is, for example, an optical recording medium such as a digital versatile disc (DVD) or a phase change rewritable disk (PD), a magneto-optical recording medium such as a magneto-optical disk (MO), a tape medium, a magnetic recording medium, a semiconductor memory, or the like.

For example, in a case where the computer 1000 functions as the medical image generation apparatus 100 according to the embodiment, the CPU 1100 of the computer 1000 executes a program loaded on the RAM 1200 to implement the functions of the acquisition unit 131, the calculation unit 132, the setting unit 133, the generation unit 134, the provision unit 135, and the like. The CPU 1100 of the computer 1000 reads and executes these programs from the recording medium 1800, but as another example, may acquire these programs from another device via a predetermined communication network. In addition, the HDD 1400 stores a medical image generation program according to the present disclosure and data in the storage unit 120.

7. Others

In addition, among the processes described in the above embodiments and modifications, all or part of the processes described as being automatically performed can be manually performed, or all or part of the processes described as being manually performed can be automatically performed by a known method. In addition, the processing procedure, specific name, and information including various pieces of data and parameters illustrated in the document and the drawings can be arbitrarily changed unless otherwise specified. For example, the various types of information illustrated in each figure are not limited to the illustrated information.

In addition, each component of each device illustrated in the drawings is functionally conceptual, and is not necessarily physically configured as illustrated in the drawings. That is, a specific form of distribution and integration of each device is not limited to the illustrated form, and all or part thereof can be functionally or physically distributed and integrated in an arbitrary unit according to various loads, usage conditions, and the like.

In addition, the above-described embodiments and modifications can be appropriately combined within a range that does not contradict processing contents.

Although some of the embodiments of the present application have been described in detail with reference to the drawings, they are merely examples, and the present invention can be implemented in other forms subjected to various modifications and improvements on the basis of the knowledge of those skilled in the art, including the aspects described in the disclosure of the invention.

In addition, the "section, module, unit" described above can be read as "means", "circuit", or the like. For example, the acquisition unit can be replaced with an acquisition means or an acquisition circuit.

Note that the present technology can also have the following configurations.

(1) A medical image generation apparatus including
an acquisition unit configured to acquire a first medical image captured with fluorescence of a predetermined wavelength and a second medical image captured with fluorescence of a wavelength different from the predetermined wavelength,
a calculation unit configured to calculate a degree of scattering indicating a degree of blur of fluorescence, of a living body, included in the first medical image and the second medical image acquired by the acquisition unit, and
a generation unit configured to generate an output image on the basis of at least either one of degrees of scattering calculated by the calculation unit.

(2) The medical image generation apparatus according to (1), in which
the acquisition unit
acquires the second medical image captured with fluorescence of a wavelength longer than the predetermined wavelength and the first medical image captured with fluorescence of the predetermined wavelength shorter than the wavelength of fluorescence of the long wavelength.

(3) The medical image generation apparatus according to (1) or (2), in which
the generation unit
generates the output image on the basis of a difference between a first degree of scattering that is a degree of scattering of the first medical image and a second degree of scattering that is a degree of scattering of the second medical image.

(4) The medical image generation apparatus according to any one of (1) to (3) further including
a setting unit configured to set, by applying to one of the first medical image and the second medical image, a filter coefficient for reproducing a first degree of scattering that is a degree of scattering of the first medical image or a second degree of scattering that is a degree of scattering of the second medical image, the filter coefficient being for the other of the first medical image and the second medical image, in which
the generation unit
generates the output image on the basis of a filter coefficient set by the setting unit and the first medical image.

(5) The medical image generation apparatus according to (4), in which the setting unit sets the filter coefficient for reproducing the second degree of scattering in the first medical image by applying to the first medical image having a larger degree of scattering than the second medical image.

(6) The medical image generation apparatus according to (4), in which
the setting unit
sets an inverse filter coefficient based on the filter coefficient for reproducing the first degree of scattering in the second medical image by applying to the second medical image having a smaller degree of scattering than the first medical image, and
the generation unit generates the output image on the basis of the inverse filter coefficient set by the setting unit and the first medical image.

(7) The medical image generation apparatus according to (6), in which
the setting unit
sets an inverse filter coefficient based on the filter coefficient that minimizes a difference between the first degree of scattering and the second degree of scattering among a plurality of the second degrees of scattering reproduced by applying to the second medical image having a smaller degree of scattering than the first medical image.

(8) The medical image generation apparatus according to (3), in which
the generation unit
generates the output image on the basis of a combination ratio for combining the first medical image with the second medical image on the basis of the first degree of scattering and the second degree of scattering.

(9) The medical image generation apparatus according to (8), in which
the generation unit
generates the output image according to a difference between the first degree of scattering and the second degree of scattering.

(10) The medical image generation apparatus according to any one of (1) to (9), in which
the calculation unit
calculates a scattering suppression effect value indicating an effect of suppressing scattering of fluorescence on the basis of information regarding a difference between a first degree of scattering that is a degree of scattering of the first medical image and a second degree of scattering that is a degree of scattering of the second medical image, and
the medical image generation apparatus further includes a provision unit configured to provide, on the basis of the scattering suppression effect value calculated by the calculation unit, the output image to which information for displaying in a visible state an effect in which scattering of fluorescence is suppressed is added.

(11) The medical image generation apparatus according to any one of (1) to (10), in which
the calculation unit
calculates a degree of scattering of a medical image for each region corresponding to an identical position information included in the first medical image and the second medical image.

(12) The medical image generation apparatus according to any one of (1) to (11), in which
the calculation unit
calculates a degree of scattering of a medical image for each pixel corresponding to an identical position information included in the first medical image and the second medical image.

(13) The medical image generation apparatus according to any one of (1) to (12), in which
the acquisition unit
acquires the first medical image and the second medical image captured with fluorescence by indocyanine green (ICG), 5-Ala (PpIX), or fluorescein as the fluorescence, and
the generation unit
generates the output image for fluorescence observation with the ICG, the 5-Ala (PpIX), or the fluorescein.

(14) A medical image generation method executed by a computer, the method including
an acquisition step of acquiring a first medical image captured with fluorescence of a predetermined wavelength and a second medical image captured with fluorescence of a wavelength different from the predetermined wavelength,
a calculation step of calculating a degree of scattering indicating a degree of blur of fluorescence, of a living body, included in the first medical image and the second medical image acquired by the acquisition step, and
a generation step of generating an output image on the basis of at least either one of degrees of scattering calculated by the calculation step.

(15) A medical image generation program causing a computer to execute
an acquisition step of acquiring a first medical image captured with fluorescence of a predetermined wavelength and a second medical image captured with fluorescence of a wavelength different from the predetermined wavelength,
a calculation step of calculating a degree of scattering indicating a degree of blur of fluorescence, of a living body, included in the first medical image and the second medical image acquired by the acquisition step, and
a generation step of generating an output image on the basis of at least either one of degrees of scattering calculated by the calculation step.

REFERENCE SIGNS LIST

1 Medical image generation system
10 Imaging unit
11 Light source
12 Filter
13 Imaging element
100 Medical image generation apparatus (200, 300, 400)
110 Communication unit
120 Storage unit
130 Control unit (230, 330, 430)
131 Acquisition unit
132 Calculation unit
133 Setting unit
134 Generation unit
135 Provision unit
233 Derivation unit
435 Visualization unit
N Network

The invention claimed is:
1. A medical image generation apparatus comprising:
circuitry configured to:
acquire a first medical image captured with fluorescence of a predetermined wavelength and a second medical image captured with fluorescence of a wavelength different from the predetermined wavelength;
calculate a degree of scattering indicating a degree of blur of fluorescence, of a living body, included in the first medical image and the second medical image acquired; and
generate an output image on a basis of a difference between a first degree of scattering that is a degree of scattering of the first medical image and a second degree of scattering that is a degree of scattering of the second medical image.

2. The medical image generation apparatus according to claim 1, wherein the circuitry is configured to:
acquire the second medical image captured with fluorescence of a wavelength longer than the predetermined wavelength and the first medical image captured with fluorescence of the predetermined wavelength shorter than the wavelength of fluorescence of the long wavelength.

3. The medical image generation apparatus according to claim 1, wherein the circuitry is configured to:
generate the output image on a basis of a combination ratio for combining the first medical image with the second medical image on a basis of the first degree of scattering and the second degree of scattering.

4. The medical image generation apparatus according to claim 3, wherein the circuitry is configured to:
generate the output image according to a difference between the first degree of scattering and the second degree of scattering.

5. The medical image generation apparatus according to claim 1, wherein the circuitry is configured to:
calculate a scattering suppression effect value indicating an effect of suppressing scattering of fluorescence on a basis of information regarding a difference between a first degree of scattering that is a degree of scattering of the first medical image and a second degree of scattering that is a degree of scattering of the second medical image, and
provide, on a basis of the scattering suppression effect value calculated, the output image to which information for displaying in a visible state an effect in which scattering of fluorescence is suppressed is added.

6. The medical image generation apparatus according to claim 1, wherein
the circuitry is configured to
calculate a degree of scattering of a medical image for each region corresponding to an identical position information included in the first medical image and the second medical image.

7. The medical image generation apparatus according to claim 1, wherein the circuitry is configured to:
calculate a degree of scattering of a medical image for each pixel corresponding to an identical position information included in the first medical image and the second medical image.

8. The medical image generation apparatus according to claim 1, wherein the circuitry is configured to:
acquire the first medical image and the second medical image captured with fluorescence by indocyanine green (ICG), 5-Ala (PpIX), or fluorescein as the fluorescence, and
generate the output image for fluorescence observation with the ICG, the 5-Ala (PpIX), or the fluorescein.

9. A medical image generation apparatus according comprising:
circuitry configured to
acquire a first medical image captured with fluorescence of a predetermined wavelength and a second medical image captured with fluorescence of a wavelength different from the predetermined wavelength;
calculate a degree of scattering indicating a degree of blur of fluorescence, of a living body, included in the first medical image and the second medical image acquired;
set, by applying to one of the first medical image and the second medical image, a filter coefficient for reproducing a first degree of scattering that is a degree of scattering of the first medical image or a second degree of scattering that is a degree of scattering of the second medical image, the filter coefficient being for the other of the first medical image and the second medical image; and
generate an output image on a basis of a filter coefficient set and the first medical image.

10. The medical image generation apparatus according to claim 9, wherein the circuitry is configured to:
set the filter coefficient for reproducing the second degree of scattering in the first medical image by applying to the first medical image having a larger degree of scattering than the second medical image.

11. The medical image generation apparatus according to claim 9, wherein the circuitry is configured to:
set an inverse filter coefficient based on the filter coefficient for reproducing the first degree of scattering in the second medical image by applying to the second medical image having a smaller degree of scattering than the first medical image, and
generate the output image on a basis of the inverse filter coefficient set and the first medical image.

12. The medical image generation apparatus according to claim 11, wherein the circuitry is configured to:
set an inverse filter coefficient based on the filter coefficient that minimizes a difference between the first degree of scattering and the second degree of scattering among a plurality of the second degrees of scattering reproduced by applying to the second medical image having a smaller degree of scattering than the first medical image.

13. A medical image generation method executed by a computer, the method comprising:
acquiring a first medical image captured with fluorescence of a predetermined wavelength and a second medical image captured with fluorescence of a wavelength different from the predetermined wavelength;
calculating a degree of scattering indicating a degree of blur of fluorescence, of a living body, included in the first medical image and the second medical image acquired; and
of generating an output image on a basis of a difference between a first degree of scattering that is a degree of scattering of the first medical image and a second degree of scattering that is a degree of scattering of the second medical image.

14. The medical image generation method according to claim 13, further comprising
generating the output image on a basis of a combination ratio for combining the first medical image with the second medical image on a basis of the first degree of scattering and the second degree of scattering.

15. The medical image generation method according to claim 14, further comprising generating the output image according to a difference between the first degree of scattering and the second degree of scattering.

16. A medical image generation program stored on a non-transitory computer readable storage device, the program causing a computer to execute:
acquiring a first medical image captured with fluorescence of a predetermined wavelength and a second medical image captured with fluorescence of a wavelength different from the predetermined wavelength;
calculating a degree of scattering indicating a degree of blur of fluorescence, of a living body, included in the first medical image and the second medical image acquired;

setting, by applying to one of the first medical image and the second medical image, a filter coefficient for reproducing a first degree of scattering that is a degree of scattering of the first medical image or a second degree of scattering that is a degree of scattering of the second medical image, the filter coefficient being for the other of the first medical image and the second medical image; and generating an output image on a basis of the filter coefficient set and the first medical image.

17. The medical image generation program according to claim 16, wherein the program causing the computer to execute:

setting the filter coefficient for reproducing the second degree of scattering in the first medical image by applying to the first medical image having a larger degree of scattering than the second medical image.

18. The medical image generation program according to claim 16, wherein the program causing the computer to execute:

setting an inverse filter coefficient based on the filter coefficient for reproducing the first degree of scattering in the second medical image by applying to the second medical image having a smaller degree of scattering than the first medical image, and generating the output image on a basis of the inverse filter coefficient set and the first medical image.

19. The medical image generation program according to claim 18, wherein the program causing the computer to execute:

setting an inverse filter coefficient based on the filter coefficient that minimizes a difference between the first degree of scattering and the second degree of scattering among a plurality of the second degrees of scattering reproduced by applying to the second medical image having a smaller degree of scattering than the first medical image.

20. The medical image generation program according to claim 16, wherein the program causing the computer to execute:

calculating a scattering suppression effect value indicating an effect of suppressing scattering of fluorescence on a basis of information regarding the difference between the first degree of scattering and the second degree of scattering, and providing, on a basis of the scattering suppression effect value calculated, the output image to which information for displaying in a visible state an effect in which scattering of fluorescence is suppressed is added.

* * * * *